US009072821B2

(12) United States Patent
Van Epps et al.

(10) Patent No.: US 9,072,821 B2
(45) Date of Patent: Jul. 7, 2015

(54) BIOCOMPATIBLE STRUCTURES AND COMPOSITIONS

(75) Inventors: Dennis E. Van Epps, Goleta, CA (US); Alexei Goraltchouk, Goleta, CA (US); Cindy D. Ren, Los Angeles, CA (US); Jordan M. Thompson, Scotts Valley, CA (US)

(73) Assignee: Allergan, Inc., Irvine, CA (US)

( * ) Notice: Subject to any disclaimer, the term of this patent is extended or adjusted under 35 U.S.C. 154(b) by 410 days.

(21) Appl. No.: 13/021,615

(22) Filed: Feb. 4, 2011

(65) Prior Publication Data

US 2011/0196489 A1    Aug. 11, 2011

Related U.S. Application Data

(60) Provisional application No. 61/301,864, filed on Feb. 5, 2010.

(51) Int. Cl.
| | |
|---|---|
| *A61F 2/12* | (2006.01) |
| *A61L 2/02* | (2006.01) |
| *A61L 27/56* | (2006.01) |
| *A61L 27/34* | (2006.01) |

(52) U.S. Cl.
CPC . *A61L 27/56* (2013.01); *A61F 2/12* (2013.01); *Y10T 428/26* (2015.01); *Y10T 428/269* (2015.01); *A61L 27/34* (2013.01); *A61L 2430/04* (2013.01)

(58) Field of Classification Search
CPC .......... A61F 2/12; A61F 2/52; A61L 2430/04
USPC ........ 623/1.39–1.4, 7–8, 23.51, 23.55, 23.58, 623/23.6–23.63, 23.66, 23.7, 23.72–23.74; 521/65
See application file for complete search history.

(56) References Cited

U.S. PATENT DOCUMENTS

| | | | |
|---|---|---|---|
| 2,805,208 A | 9/1957 | Roche | |
| 3,189,921 A | 6/1965 | Pangman | |
| 3,293,663 A | 12/1966 | Cronin | |
| 3,366,975 A | 2/1968 | Pangman | |
| 3,559,214 A | 2/1971 | Pangman | |
| 3,600,718 A | 8/1971 | Boone | |
| 3,665,520 A | 5/1972 | Perras | |
| 3,700,380 A | 10/1972 | Kitrilakis | |
| 3,852,832 A | 12/1974 | McGhan | |
| 3,934,274 A | 1/1976 | Hartley, Jr. | |
| 4,019,499 A | 4/1977 | Fitzgerald | |

(Continued)

FOREIGN PATENT DOCUMENTS

| | | |
|---|---|---|
| EP | 0230672 | 8/1987 |
| EP | 0315814 | 5/1989 |

(Continued)

OTHER PUBLICATIONS

Alvarez, Sonia et al., "Synthesis of Macro/Mesoporous Silica and Carbon Monoliths by Using a Commercial Polyurethane Foam as Sacrificial Template", Materials Letters, 61, 2378-2381 (2007).
Barr, S. et al., "Current Implant Surface Technology: An Examination of Their Nanostructure and Their Influence on Fibroblast Alignment and Biocompatibility", Elastic, 2009, 9, 198-217.
Barnsley, Philip et al., "Textured Surface Breast Implants in the Prevention of Capsular Contracture Among Breast Augmentation Patients: A Meta-Analysis of Randomized Controlled Trials", Plastic and Reconstructive Surgery, 2006, 117(7), 2182-2190.
Inamed Aesthetics Brochure, Directions for Use Style 410 Silicone-Filled Breast Implants (2003).
Ma, Peter, "Scaffolds for tissue fabrication", Materials Today, 2004, 7, 30-40.

(Continued)

*Primary Examiner* — Andrew Iwamaye
(74) *Attorney, Agent, or Firm* — Linda Allyson Nassif

(57) ABSTRACT

Described herein are material compositions including various textures which when implanted in a mammal encourage an optimal biological response.

4 Claims, 14 Drawing Sheets

(56) References Cited

U.S. PATENT DOCUMENTS

| | | |
|---|---|---|
| 4,034,751 A | 7/1977 | Hung |
| 4,157,085 A | 6/1979 | Austad |
| 4,231,979 A | 11/1980 | White |
| 4,264,990 A | 5/1981 | Hamas |
| 4,298,997 A | 11/1981 | Rybka |
| 4,298,998 A | 11/1981 | Naficy |
| 4,329,385 A | 5/1982 | Banks |
| 4,428,082 A | 1/1984 | Naficy |
| 4,433,440 A | 2/1984 | Cohen |
| 4,470,160 A | 9/1984 | Cavon |
| 4,482,577 A | 11/1984 | Goldstein |
| 4,499,211 A | 2/1985 | Walch |
| 4,531,244 A | 7/1985 | Hamas |
| 4,573,999 A | 3/1986 | Netto |
| 4,584,324 A | 4/1986 | Bauman et al. |
| 4,592,755 A | 6/1986 | Penton |
| 4,610,690 A | 9/1986 | Tiffamy |
| 4,631,296 A | 12/1986 | Bauman et al. |
| 4,636,213 A | 1/1987 | Pakiam |
| 4,643,733 A | 2/1987 | Becker |
| 4,647,618 A | 3/1987 | Bauman et al. |
| 4,648,880 A | 3/1987 | Brauman |
| 4,650,487 A | 3/1987 | Chaglassian |
| 4,651,717 A | 3/1987 | Jakubczak |
| 4,681,587 A | 7/1987 | Eberl |
| 4,740,208 A | 4/1988 | Cavon |
| 4,772,285 A | 9/1988 | Ksander |
| 4,773,908 A | 9/1988 | Becker |
| 4,773,909 A | 9/1988 | Chaglassian |
| 4,790,848 A | 12/1988 | Cronin |
| 4,795,464 A | 1/1989 | Eberl |
| 4,803,025 A | 2/1989 | Brockmeyer |
| 4,828,560 A | 5/1989 | Heyler |
| 4,840,628 A | 6/1989 | Cavon |
| 4,841,992 A | 6/1989 | Sasaki |
| 4,859,383 A | 8/1989 | Dillon |
| 4,859,712 A | 8/1989 | Cox |
| 4,889,744 A | 12/1989 | Quaid |
| 4,899,764 A | 2/1990 | Gauger |
| 4,902,294 A | 2/1990 | Gosserez |
| 4,906,423 A | 3/1990 | Frisch |
| 4,936,858 A | 6/1990 | O'Keeffe |
| 4,944,749 A | 7/1990 | Becker |
| 4,944,750 A | 7/1990 | Cox, Jr. |
| 4,950,292 A | 8/1990 | Audretsch |
| 4,955,907 A | 9/1990 | Ledergerber |
| 4,955,909 A | 9/1990 | Ersek |
| 4,960,425 A | 10/1990 | Yan |
| 4,965,430 A | 10/1990 | Curtis |
| 4,969,899 A | 11/1990 | Cox, Jr. |
| 5,002,572 A | 3/1991 | Picha |
| 5,007,929 A * | 4/1991 | Quaid ............................. 623/8 |
| 5,007,940 A | 4/1991 | Berg |
| 5,011,494 A | 4/1991 | von Recum et al. |
| 5,022,942 A | 6/1991 | Yan |
| 5,026,394 A | 6/1991 | Baker |
| 5,034,422 A | 7/1991 | Triolo |
| 5,035,249 A | 7/1991 | Sasaki |
| 5,092,348 A | 3/1992 | Dubrul |
| 5,092,882 A | 3/1992 | Lynn |
| 5,104,409 A | 4/1992 | Baker |
| 5,116,387 A | 5/1992 | Berg |
| 5,135,959 A | 8/1992 | Hill |
| 5,146,933 A | 9/1992 | Boyd |
| 5,147,398 A | 9/1992 | Lynn |
| 5,158,571 A | 10/1992 | Picha |
| 5,158,573 A | 10/1992 | Berg |
| 5,171,269 A | 12/1992 | Bark |
| 5,185,297 A | 2/1993 | Park |
| 5,207,709 A | 5/1993 | Picha |
| 5,219,361 A | 6/1993 | von Recum et al. |
| 5,236,453 A | 8/1993 | Picha |
| 5,236,454 A | 8/1993 | Miller |
| 5,236,457 A | 8/1993 | Devanathan |
| 5,246,454 A | 9/1993 | Petersen |
| 5,282,856 A | 2/1994 | Ledergerber |
| 5,296,069 A | 3/1994 | Robert |
| 5,348,788 A | 9/1994 | White |
| 5,354,338 A | 10/1994 | Ledergerber |
| 5,358,521 A | 10/1994 | Shane |
| 5,376,117 A | 12/1994 | Pinchuk |
| 5,383,929 A | 1/1995 | Ledergerber |
| 5,437,824 A | 8/1995 | Carlisle |
| 5,441,919 A | 8/1995 | Park |
| 5,447,535 A | 9/1995 | Muller |
| 5,455,100 A | 10/1995 | White |
| 5,480,430 A | 1/1996 | Carlisle |
| 5,496,367 A | 3/1996 | Fisher |
| 5,496,370 A | 3/1996 | Hamas |
| 5,507,808 A | 4/1996 | Becker |
| 5,522,896 A | 6/1996 | Prescott |
| 5,525,275 A | 6/1996 | Iverson |
| 5,534,023 A | 7/1996 | Henley |
| 5,545,217 A | 8/1996 | Offray |
| 5,545,220 A | 8/1996 | Andrews |
| 5,549,671 A | 8/1996 | Waybright |
| 5,571,179 A | 11/1996 | Manders |
| RE35,391 E | 12/1996 | Brauman |
| 5,589,176 A | 12/1996 | Seare |
| 5,605,693 A | 2/1997 | Seare |
| 5,607,473 A | 3/1997 | Weber-Unger |
| 5,624,674 A | 4/1997 | Seare |
| 5,630,843 A | 5/1997 | Rosenberg |
| 5,630,844 A | 5/1997 | Dogan |
| 5,653,755 A | 8/1997 | Ledergerber |
| 5,658,330 A | 8/1997 | Carlisle |
| 5,674,285 A | 10/1997 | Quaid |
| 5,681,572 A | 10/1997 | Seare, Jr. |
| 5,779,734 A | 7/1998 | Ledergerber |
| 5,798,065 A | 8/1998 | Picha |
| 5,824,081 A | 10/1998 | Knapp |
| 5,843,189 A | 12/1998 | Perouse |
| 5,855,588 A | 1/1999 | Young |
| 5,871,497 A | 2/1999 | Young |
| 5,895,423 A | 4/1999 | Becker |
| 5,935,164 A | 8/1999 | Iversen |
| 5,954,910 A | 9/1999 | Kikukawa et al. |
| 5,961,552 A | 10/1999 | Iversen |
| 5,964,803 A | 10/1999 | Iversen |
| 5,965,076 A | 10/1999 | Banks |
| 5,984,943 A | 11/1999 | Young |
| 6,071,309 A | 6/2000 | Knowlton |
| 6,074,421 A | 6/2000 | Murphy |
| 6,083,262 A | 7/2000 | Caravel |
| 6,099,565 A | 8/2000 | Sakura |
| 6,113,634 A | 9/2000 | Weber-Unger |
| 6,146,418 A | 11/2000 | Berman |
| 6,183,514 B1 | 2/2001 | Becker |
| 6,187,043 B1 | 2/2001 | Ledergerber |
| 6,203,570 B1 | 3/2001 | Baeke |
| 6,206,930 B1 | 3/2001 | Burg |
| 6,214,045 B1 | 4/2001 | Corbitt, Jr. |
| 6,214,926 B1 | 4/2001 | Winn |
| 6,315,796 B1 | 11/2001 | Eaton |
| 6,340,648 B1 * | 1/2002 | Imura et al. ..................... 501/80 |
| 6,387,133 B1 | 5/2002 | Perouse |
| 6,432,138 B1 | 8/2002 | Offray |
| 6,464,726 B1 | 10/2002 | Heljenek |
| 6,520,989 B1 | 2/2003 | Eaton |
| 6,531,523 B1 | 3/2003 | Davankov |
| 6,544,287 B1 | 4/2003 | Johnson |
| 6,596,404 B1 | 7/2003 | Albaugh et al. |
| 6,602,452 B2 | 8/2003 | Schuessler |
| 6,605,116 B2 | 8/2003 | Falcon |
| 6,638,308 B2 | 10/2003 | Corbitt, Jr. |
| 6,673,285 B2 | 1/2004 | Ma |
| 6,692,527 B1 | 2/2004 | Bellin |
| 6,755,861 B2 | 6/2004 | Nakao |
| 6,802,861 B1 | 10/2004 | Hamas |
| 6,811,570 B1 | 11/2004 | Gehl |
| 6,818,673 B2 | 11/2004 | Ferguson |
| 6,875,233 B1 | 4/2005 | Turner |
| 6,881,226 B2 | 4/2005 | Corbitt, Jr. |
| 6,900,055 B1 | 5/2005 | Fuller |

(56) References Cited

U.S. PATENT DOCUMENTS

| | | | |
|---|---|---|---|
| 6,913,626 B2 | 7/2005 | McGhan | |
| 6,916,339 B1 | 7/2005 | Missana | |
| 6,921,418 B2 | 7/2005 | Ledergerber | |
| 6,932,840 B1 | 8/2005 | Bretz | |
| 7,081,135 B2 | 7/2006 | Smith et al. | |
| 7,081,136 B1 | 7/2006 | Becker | |
| 7,105,116 B2 | 9/2006 | Bellin | |
| 7,169,180 B2 | 1/2007 | Brennan | |
| 7,192,450 B2 | 3/2007 | Brauker | |
| 7,244,270 B2 | 7/2007 | Lesh | |
| 7,323,208 B2 | 1/2008 | Ma | |
| 7,476,249 B2 | 1/2009 | Frank | |
| 7,520,896 B2 | 4/2009 | Benslimane | |
| 7,547,393 B2 | 6/2009 | Ramaswamy | |
| 7,625,405 B2 | 12/2009 | Purkait | |
| 7,632,228 B2 | 12/2009 | Brauker | |
| 7,632,291 B2 | 12/2009 | Stephens | |
| 7,641,688 B2 | 1/2010 | Lesh | |
| 7,645,475 B2 | 1/2010 | Prewett | |
| 8,202,317 B2 | 6/2012 | Becker | |
| 8,313,527 B2 | 11/2012 | Powell et al. | |
| 2002/0038147 A1 | 3/2002 | Miller | |
| 2002/0193885 A1 | 12/2002 | Legeay | |
| 2003/0036803 A1 | 2/2003 | McGhan | |
| 2003/0093151 A1 | 5/2003 | Zhang | |
| 2003/0105469 A1 | 6/2003 | Karmon | |
| 2003/0205846 A1 | 11/2003 | Bellin | |
| 2003/0208269 A1 | 11/2003 | Eaton | |
| 2004/0010225 A1 | 1/2004 | Schuessler | |
| 2004/0115241 A1 | 6/2004 | Calhoun | |
| 2004/0127985 A1 | 7/2004 | Bellin | |
| 2004/0143327 A1 | 7/2004 | Ku | |
| 2004/0148024 A1 | 7/2004 | Williams | |
| 2004/0153151 A1 | 8/2004 | Gonzalez | |
| 2004/0176493 A1 | 9/2004 | Ferguson | |
| 2004/0213986 A1 | 10/2004 | Kim | |
| 2005/0055093 A1 | 3/2005 | Brennan | |
| 2005/0070124 A1 | 3/2005 | Miller | |
| 2005/0112169 A1 | 5/2005 | Brauker | |
| 2005/0122169 A1 | 6/2005 | Watanabe | |
| 2005/0196452 A1 | 9/2005 | Boyan et al. | |
| 2005/0216094 A1* | 9/2005 | Prewett | 623/23.74 |
| 2005/0251083 A1* | 11/2005 | Carr-Brendel et al. | 602/41 |
| 2006/0002810 A1* | 1/2006 | Grohowski, Jr. | 419/2 |
| 2006/0036266 A1 | 2/2006 | Sulmanidze et al. | |
| 2006/0036320 A1 | 2/2006 | Job | |
| 2006/0136056 A1 | 6/2006 | Wohl | |
| 2006/0224239 A1 | 10/2006 | Tiahrt | |
| 2006/0229721 A1 | 10/2006 | Ku | |
| 2006/0235094 A1 | 10/2006 | Habibi-Naini | |
| 2006/0246121 A1 | 11/2006 | Ma | |
| 2007/0005140 A1* | 1/2007 | Kim et al. | 623/17.16 |
| 2007/0093911 A1 | 4/2007 | Fricke | |
| 2007/0093912 A1* | 4/2007 | Borden | 623/23.75 |
| 2007/0104693 A1 | 5/2007 | Quijano | |
| 2007/0104695 A1 | 5/2007 | Quijano | |
| 2007/0116735 A1 | 5/2007 | Calhoun | |
| 2007/0135916 A1 | 6/2007 | Maxwell | |
| 2007/0154525 A1 | 7/2007 | Calhoun | |
| 2007/0190108 A1 | 8/2007 | Datta et al. | |
| 2007/0198085 A1 | 8/2007 | Benslimane | |
| 2008/0009830 A1 | 1/2008 | Fujimoto | |
| 2008/0071371 A1 | 3/2008 | Elshout | |
| 2008/0075752 A1 | 3/2008 | Ratner | |
| 2008/0154366 A1 | 6/2008 | Frank | |
| 2008/0241212 A1 | 10/2008 | Moses | |
| 2008/0268019 A1 | 10/2008 | Badylak | |
| 2008/0312739 A1 | 12/2008 | Agerup | |
| 2009/0045166 A1 | 2/2009 | Li | |
| 2009/0082864 A1 | 3/2009 | Chen | |
| 2009/0087641 A1 | 4/2009 | Favis | |
| 2009/0093878 A1 | 4/2009 | Glicksman | |
| 2009/0118829 A1 | 5/2009 | Powell | |
| 2009/0125107 A1 | 5/2009 | Maxwell | |
| 2009/0169716 A1 | 7/2009 | Linhardt | |
| 2009/0198331 A1 | 8/2009 | Kesten et al. | |
| 2009/0198332 A1 | 8/2009 | Becker | |
| 2009/0198333 A1 | 8/2009 | Becker | |
| 2010/0042211 A1 | 2/2010 | Van Epps et al. | |
| 2010/0042212 A1 | 2/2010 | Van Epps et al. | |
| 2010/0292790 A1 | 11/2010 | Stroumpoulis et al. | |
| 2011/0035004 A1 | 2/2011 | Maxwell | |
| 2011/0054605 A1 | 3/2011 | Becker | |
| 2011/0093069 A1 | 4/2011 | Goraltchouk et al. | |
| 2011/0106249 A1 | 5/2011 | Becker | |
| 2011/0117267 A1 | 5/2011 | Powell et al. | |
| 2011/0184531 A1 | 7/2011 | Goraltchouk | |
| 2011/0196488 A1 | 8/2011 | Goraltchouk et al. | |
| 2011/0276133 A1 | 11/2011 | Liu et al. | |
| 2011/0276134 A1 | 11/2011 | Manesis et al. | |
| 2011/0278755 A1 | 11/2011 | Liu et al. | |
| 2011/0282444 A1 | 11/2011 | Liu et al. | |
| 2011/0309541 A1 | 12/2011 | Thompson et al. | |
| 2011/0313073 A1 | 12/2011 | Goraltchouk et al. | |
| 2012/0004722 A1 | 1/2012 | Goraltchouk et al. | |
| 2012/0041555 A1 | 2/2012 | Manesis et al. | |
| 2012/0077010 A1 | 3/2012 | Manesis et al. | |
| 2012/0077012 A1 | 3/2012 | Liu et al. | |
| 2012/0077891 A1 | 3/2012 | Liu et al. | |
| 2012/0101574 A1 | 4/2012 | Goraltchouk et al. | |
| 2012/0142798 A1 | 6/2012 | Thompson et al. | |
| 2012/0321777 A1 | 12/2012 | Stroumpoulis et al. | |
| 2013/0013062 A1 | 1/2013 | Thompson et al. | |
| 2013/0023987 A1 | 1/2013 | Liu et al. | |
| 2013/0032962 A1 | 2/2013 | Liu et al. | |
| 2013/0053956 A1 | 2/2013 | Powell et al. | |

FOREIGN PATENT DOCUMENTS

| | | | | |
|---|---|---|---|---|
| EP | 0522585 B1 | 10/1996 | | |
| EP | 1532942 | 5/2005 | | |
| FR | 2840617 A1 * | 12/2003 | | C08J 9/28 |
| JP | 2003-062062 | 4/2003 | | |
| JP | 2007-029717 | 8/2007 | | |
| WO | WO 98/10803 | 3/1998 | | |
| WO | WO 00/24437 | 5/2000 | | |
| WO | WO 2004/037318 | 5/2004 | | |
| WO | WO 2004/062531 | 7/2004 | | |
| WO | 2006133366 | 12/2006 | | |
| WO | WO 2009/061672 | 5/2009 | | |
| WO | WO 2009/110917 | 9/2009 | | |
| WO | WO 2011/094155 | 8/2011 | | |
| WO | WO 2011/097499 | 8/2011 | | |

OTHER PUBLICATIONS

Mikes, Antonius et al., "Formation of Highly Porous Biodegradable Scaffolds for Tissue Engineering", Electronic Journal of Biotechnology, 2000, 3(2), 114-119.

Minami, Eliza et al., "The Composition and Behavior of Capsules Around Smooth and Textured Breast Implants in Pigs", Plastic and Reconstructive Surgery, 2006, 118940, 874-884.

Murphy, William et al., "Salt Fusion: An Approach to Improve Pore Interconnectivity Within Tissue Engineering Scaffolds", Tissue Engineering, vol. 8, Iss. 1, 2004.

Wei, Guobao et al., "Macroporous and Nanofibers Polymer Scaffolds and Polymer/bone-like Apatite Composite Scaffolds Generated by Sugar Spheres", Journal of Biomedical Materials Research Part A, 2006, 306-315.

Zhang, Yuan et al., "Macroporous Alumina Monoliths Prepared by Filling Polymer Foams With Alumina Hydrosols", J. Mater Sci., 44, 931-938 (2009).

Brauker et al., "Neovascularization of synthetic membranes directed by membrane microarchitecture", Journal of Biomedical Materials Research, 1995, pp. 1517-1524, vol. 29, John Wiley & Sons, Inc.

Brohim et al., "Early Tissue Reaction to Textured Breast Implant Surfaces", Anals of Plastic Surgery, 28(4): 354-362, 1992.

Sharkawy et al. "Engineering the tissue which encapsulates subcutaneous implants", II. Plasma—tissue exchange properties, 1998, pp. 586-597, John Wiley & Sons, Inc.

* cited by examiner

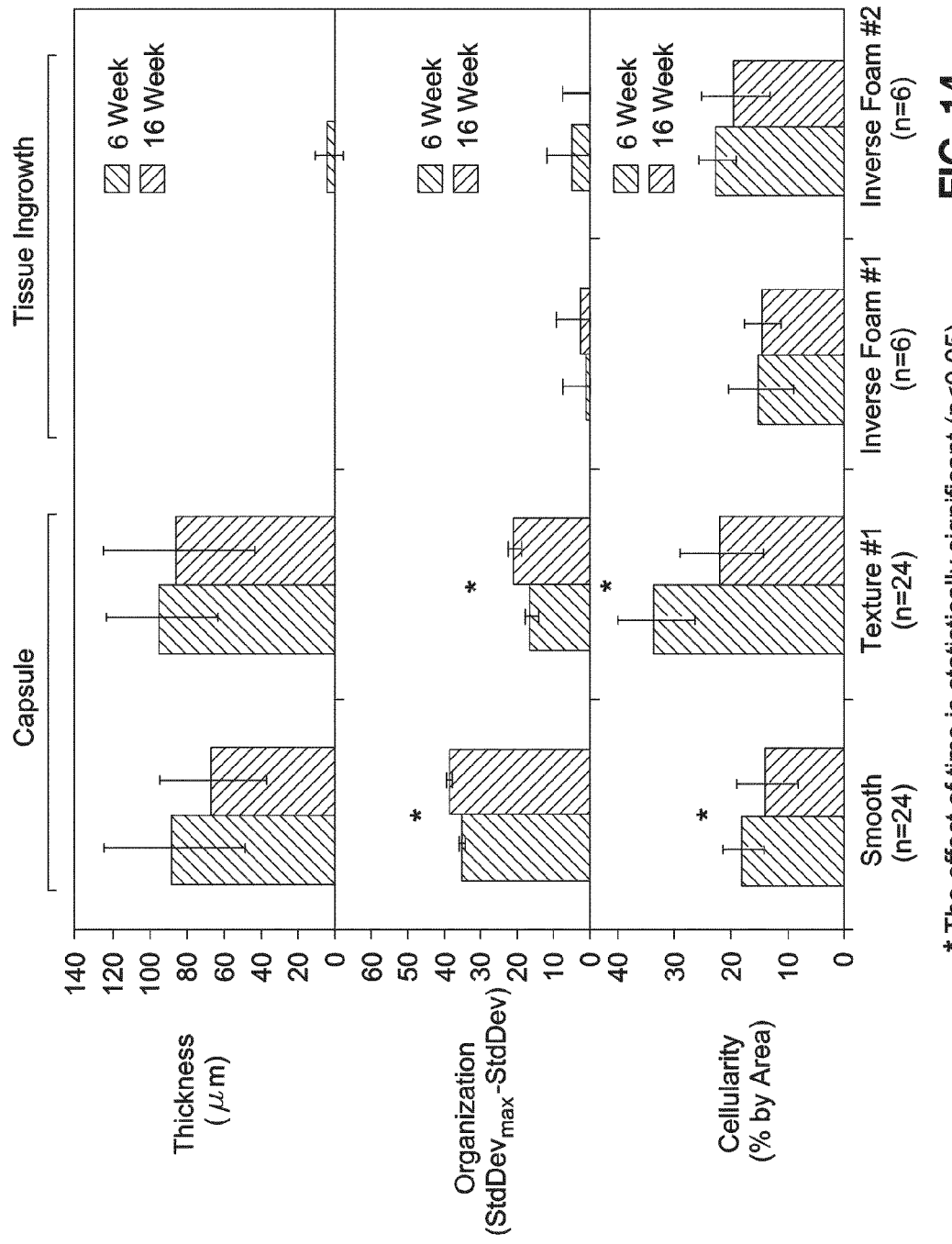

BIOCOMPATIBLE STRUCTURES AND COMPOSITIONS

RELATED APPLICATIONS

This application claims priority to U.S. Provisional Patent Application No. 61/301,864, filed on Feb. 5, 2010, the disclosure of which is incorporated herein in its entirety by this reference.

BACKGROUND

The present invention generally relates to medical implants and more specifically relates to foam-like materials suitable for implantation in a mammal.

Prostheses or implants for augmentation and/or reconstruction of the human body are well known. Capsular contracture is a complication associated with surgical implantation of prostheses, particularly with soft implants, and even more particularly, though certainly not exclusively, with fluid-filled breast implants.

Capsular contracture is believed to be a result of the immune system response to the presence of a foreign material in the body. A normal response of the body to the presence of a newly implanted object, for example a breast implant, is to form a capsule of tissue, primarily collagen fibers, around the implant. Capsular contracture occurs when the capsule begins to contract and squeeze the implant. This contracture can be discomforting or even extremely painful, and can cause distortion of the appearance of the augmented or reconstructed breast. The exact cause of contracture is not known. However, some factors may include bacterial contamination of the implant prior to placement, submuscular versus subglandular placement, and smooth surface implants versus textured surface implants, and bleeding or trauma to the area.

Surface texturing has been shown to reduce capsular contracture when compared to what are known as "smooth" surface implants. (FIGS. 1 and 2).

There is still a need for a more optimal surface textured implant that further reduces the potential for capsular contracture. The present invention addressed this need.

SUMMARY OF THE INVENTION

Described herein are microstructures and material compositions (e.g., coatings and materials) allowing soft tissue implants to obtain an optimal biological response while still attaining proper adhesion to the surrounding tissues. In one embodiment, an exemplary material is an open-cell foam having a pore size of about 10 µm to about 300 µm and an interconnection size of about 75 µm to about 300 µm, wherein the foam, upon implantation, results in an optimal biological response. In one example embodiment, the open-cell foam has a structure, for example, as illustrated in FIGS. 3, 4A and 5A.

In one embodiment, the open-cell foam is biodegradable or non-biodegradable. In some embodiments, the pore size of the open-cell foam is about 23 µm to about 102 µm. In yet another embodiment, the interconnection size of the open-cell foam is about 159 µm to about 225 µm.

In other embodiments, the open-cell foam is coated on an implantable medical device. An exemplary implantable medical device is a soft tissue implant. In one embodiment, the soft tissue implant is a breast implant.

In another embodiment, an exemplary material is an inverse foam, described elsewhere herein, having a pore size of about 400 µm to about 550 µm and an interconnection size of about 150 µm to about 300 µm, wherein the foam, upon implantation, results in substantial tissue ingrowth, minimal capsular formation and tissue adhesion. In one example embodiment, the open-cell silicone foam has a structure as illustrated in FIG. 3.

In one embodiment, the inverse foam is biodegradable or non-biodegradable. In some embodiments, the pore size of the inverse foam is about 470 µm. In yet another embodiment, the interconnection size of the inverse foam is about 210 µm.

In other embodiments, the inverse foam is coated on an implantable medical device. An exemplary implantable medical device is a soft tissue implant. In one embodiment, the soft tissue implant is a breast implant.

In another embodiment, an exemplary material is a fibrous felt, wherein the felt, upon implantation, results in substantial tissue ingrowth, minimal capsular formation and tissue adhesion. In one example embodiment, the fibrous felt has a structure as illustrated in FIG. 5A.

In one embodiment, the fibrous felt is biodegradable or non-biodegradable.

In other embodiments, the fibrous felt is coated on an implantable medical device. An exemplary implantable medical device is a soft tissue implant. In one embodiment, the soft tissue implant is a breast implant.

The said optimal biological response described herein includes at least one of substantial tissue ingrowth, minimal capsular formation and tissue adhesion.

BRIEF DESCRIPTION OF THE DRAWINGS

FIG. 14 graphically illustrates temporal changes in capsule (if present) in rat model over time.

DETAILED DESCRIPTION

Generally described herein are microstructures and material compositions (e.g., coatings) allowing soft tissue implants to obtain an optimal biological response while still attaining proper adhesion to the surrounding tissues. The optimal biological response is defined as a disorganized and thin capsule or an effectively absent capsule, with a low collagen density formed around an implant at least a portion of which is coated or formed by a material described herein. Proper adhesion to surrounding tissues is importation in that it minimizes implant rotation.

Figure 1:
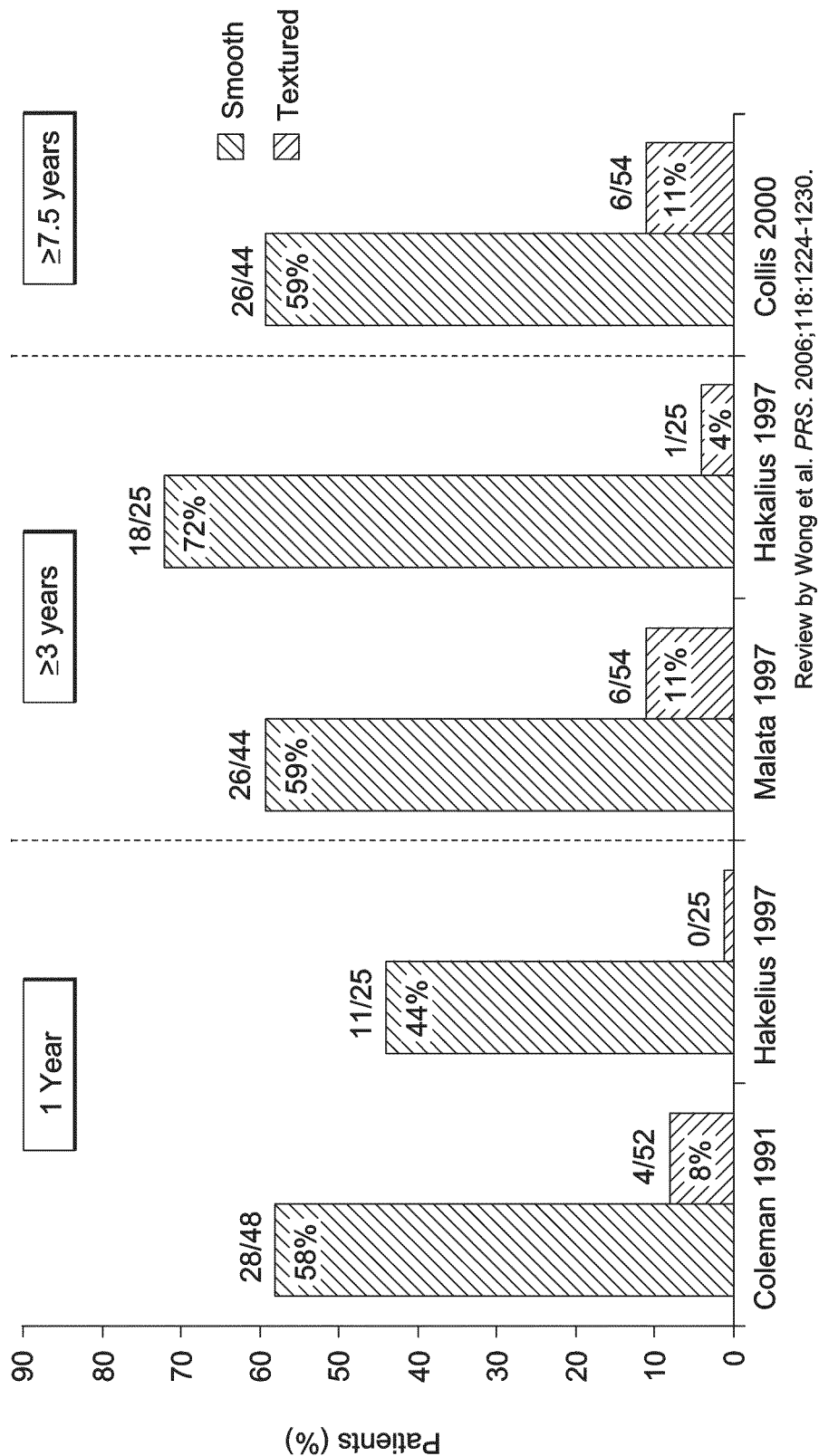
FIG. 1 graphically illustrates a comparison of capsular contracture of textured implants of the prior art versus smooth implants.
Figure 2:
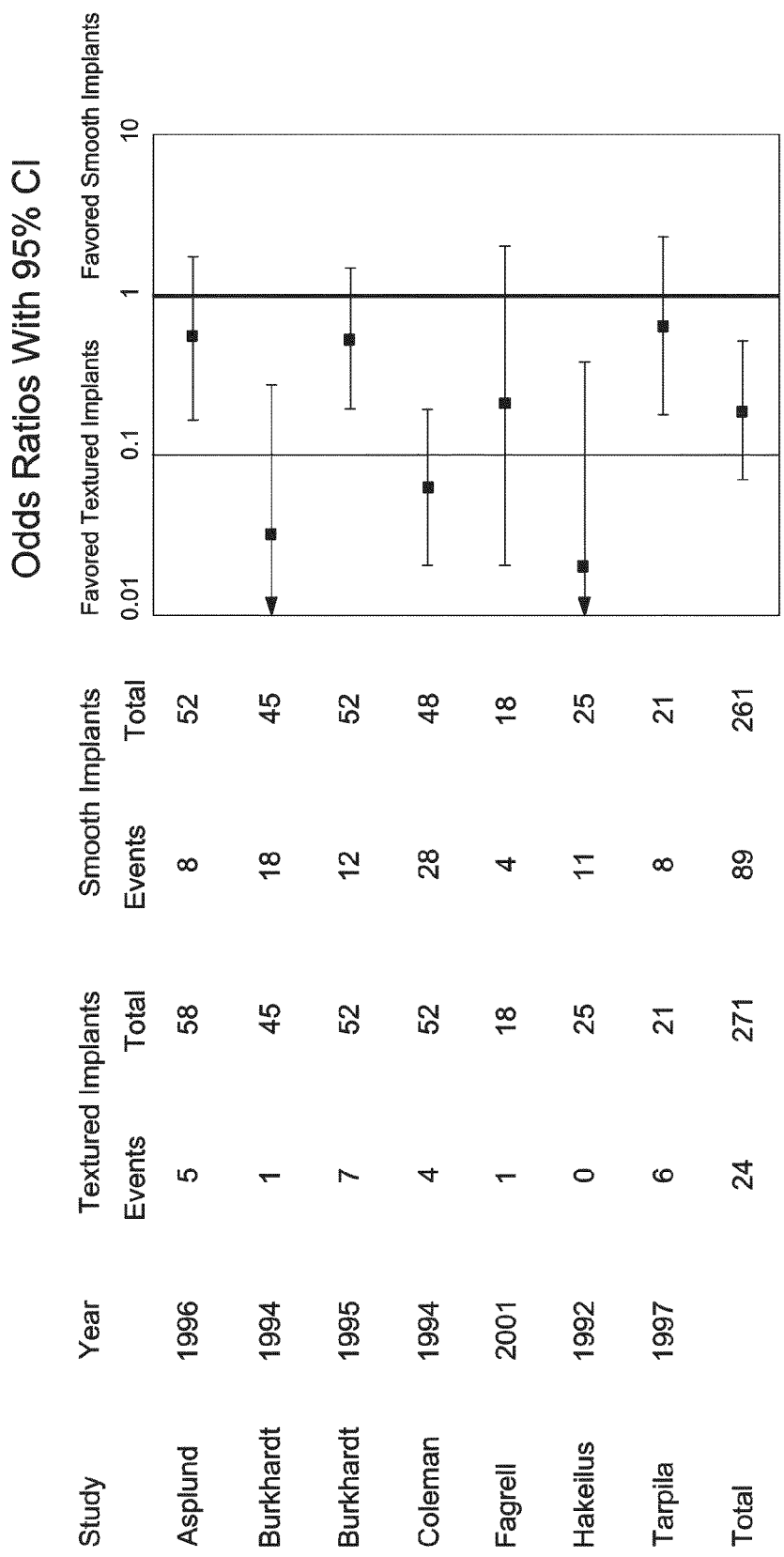
FIG. 2 illustrates odds ratios for capsular contracture in controlled trials of subglandular breast augmentation.

It is known in the art that textured implants reduce the occurrence of capsular contracture of the surrounding tissues. FIG. 1 graphically illustrates this reduction in occurrence of contracture in subglandular placed textured implants of the prior art versus smooth implants. Further, FIG. 2 illustrates the odds ratios for capsular contracture in controlled trials of subglandular breast augmentation. Based on the information in FIG. 2, a skilled artisan would appreciate that the odds of exhibiting contracture with a textured implant is less likely than it is for a smooth implant. Patients fitted with highly cohesive textured implants were less likely to exhibit contracture. However, textured implants need to be improved to allow a optimal biological response as described herein.

Three textured material geometries have been identified and are described herein producing an optimal biological response and a reduction or elimination of contracture. They are defined as an open cell foam (e.g., a classical reticulated foam geometry), an inversed foam (e.g., a matrix of interconnected spheres), and a fibrous felt structure; these are referred to herein as materials.

Figure 3:
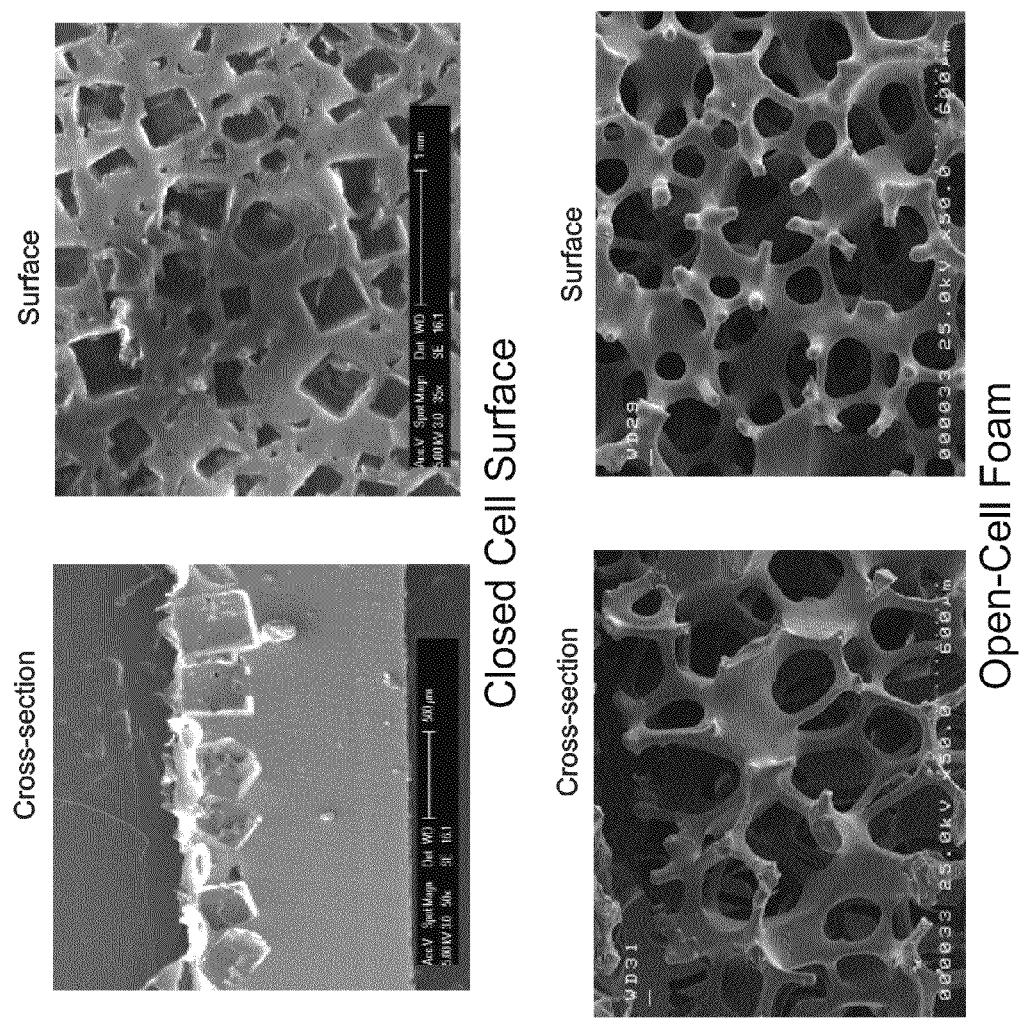
FIG. 3 illustrates a comparison of a closed-cell foam of the PRIOR ART and an open-cell foam useful in accordance with the present invention.

FIG. 3 illustrates an exemplary difference between an open-cell foam material as described herein as compared to a closed-cell or textured implant of the prior art. One skilled in the art can appreciate that the open-cell structure can allow tissue ingrowth into the void space or pores within the open-cell matrix.

The materials can have characteristics that allow the resulting implants to achieve an optimal biological response. These characteristics can include, but are not limited to appropriate thickness, sufficient porosity and pore size, sufficient pore interconnections, sufficient stiffness, strength, elasticity, exhibited abrasion resistance and reduced residuals (e.g., leachable agents).

The materials described herein can achieve an optimal biological response, for example, reduced capsule formation, while attaining proper or elevated adhesion to surrounding tissues when compared to textured materials commonly used in the art. This characteristic allows the materials to be used on a variety of implants and implant types without the drawbacks of past materials.

Figure 4A:
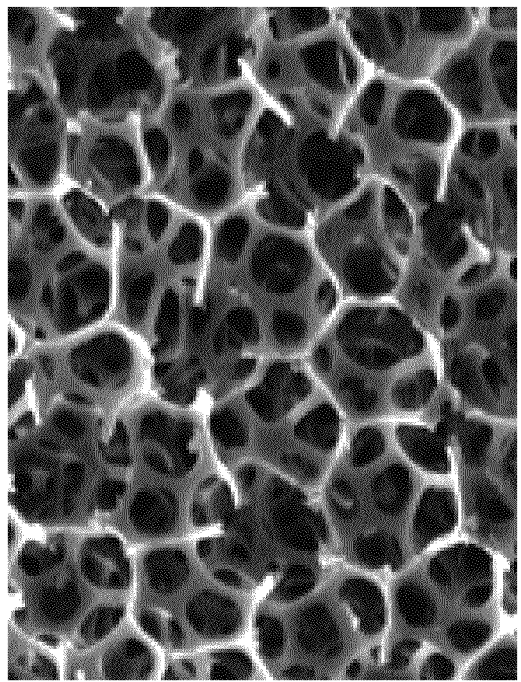
FIG. 4A is a scanning electron microscope (SEM) image at a scale of 0-600 µm of an open-cell foam according to an example embodiment described herein.
Figure 4B:
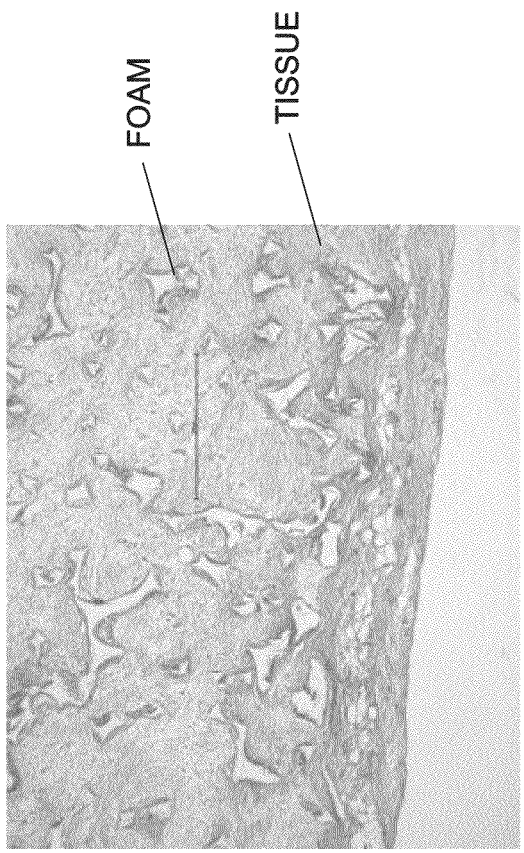
FIG. 4B is a histological image of tissue ingrowth into the open cell foam 6 weeks after subcutaneous implantation in a rat.

One class of material which can attain an optimal biological response is an open-cell foam, example, an open cell foam comprising silicone. A scanning electron microscope (SEM) image of an exemplary open-cell foam is depicted in FIG. 4A; FIG. 4B is histological image of tissue integration after 6 weeks subcutaneous implantation in a rat. Such an exemplary open-cell foam can have a pore size from about 400 µm to about 550 µm, or about 410 µm to about 530 µm, or about 450 µm to about 490 µm. In one embodiment, the pore size is about 470 µm. The open-cell foams can have an interconnection size of about 150 µm to about 300 µm, or about 175 µm to about 270 µm, or about 180 to about 240 µm. In one embodiment, the interconnection size is about 210 µm. The interconnection to pore ratio of such foams is about 44%. The interconnections to pore ratio is generally about 7.8 to about 11.4 or about 8.6 to about 10.6. In one example embodiment, the interconnections to pore ratio is about 9.6.

Figure 5B:
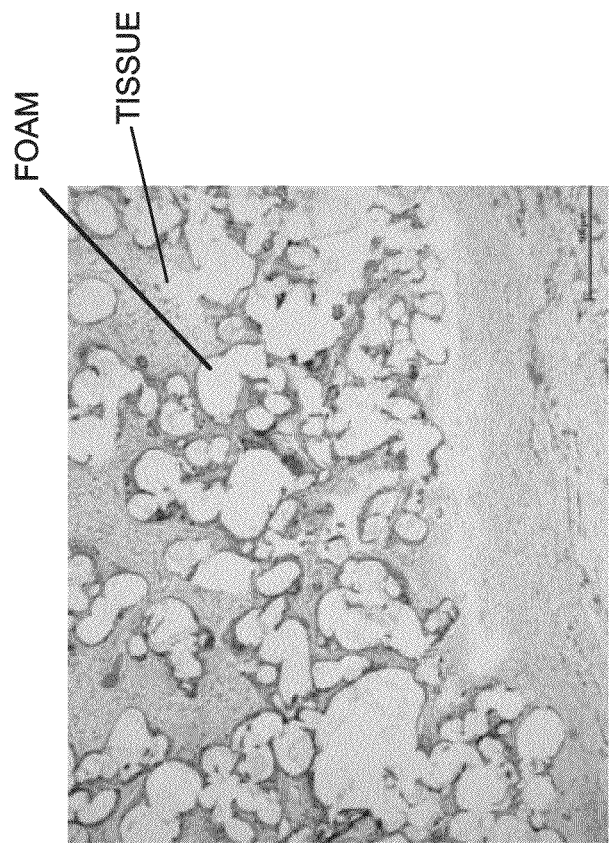
FIG. 5B is a histological image of tissue ingrowth into the open cell foam 6 weeks after subcutaneous implantation in a rat.
Figure 5A:
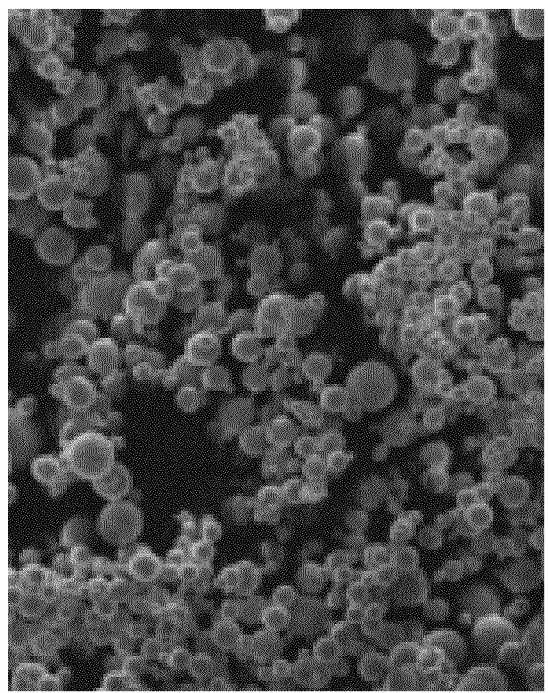
FIG. 5A is a SEM image at a scale of 0-600 µm of an inversed foam according to an example embodiment described herein.

Another type of material which can attain an optimal biological response in accordance with the invention is an inversed or inverse foam such as described in U.S. patent application Ser. No. 13/012,991, filed on Jan. 24, 2011, the entire disclosure of which is incorporated herein by this reference. An inverse foam in accordance with the invention may generally comprise interconnected microparticles or microbeads, generally made of silicone, in some cases substantially pure silicone. A scanning electron microscope (SEM) image of an exemplary inversed foam is depicted in FIG. 5A; FIG. 5B is histological image of tissue integration after 6 weeks subcutaneous implantation in a rat. Such an exemplary inversed foam can have a pore size from about 10 µm to about 300 µm, or about 15 µm to about 200 µm, or about 20 µm to about 120 µm. In one embodiment, the pore size is about 23 µm to about 102 µm. The inversed foams can have an interconnection size of about 75 µm to about 300 µm, or about 100 µm to about 270 µm, or about 150 to about 250 µm. In one embodiment, the interconnection size is about 159 µm to about 225 µm.

The inverse foams themselves can be formed of substantially pure silicone and generally comprise a highly interconnected matrix of spheres. For example, the "substantially pure" foams can include greater than about 50% silicone, greater than about 75% silicone, greater than about 90% silicone, greater than about 95% silicone or greater than about 99% silicone. The remaining component can be comprised of fused silica, other elastomers, thermoplastics or thermosets, ceramics metals, metal alloys or composites thereof.

The matrix of interconnected spheres making up the inverse foams described herein can have an associated void space within them. A theoretical void space can be a calculated void space that is dependent on the composition of the spheres themselves and the leachable agent, for example. Theoretical void space is a term of art that is well understood by those of skill in the art, and in the context of the present disclosure can be generally defined as the percentage by volume of the foam occupied by the leachable agent on a dry basis. The theoretical void space can be greater than about 50% of the foam, greater than about 75% of the foam greater than about 90% of the foam, greater than about 95% of the foam or greater than about 99% of the foams. In some embodiments, the theoretical void space can be about 50% to about 99% of the foam or about 60% to about 88% of the foams.

Tissue ingrowth occurs into the voids within the foam when the inverse foams described herein are used to coat an implantable medical device, such as a soft tissue implant. The ingrowth of tissue is intended to promote the disorganization of collagen fibers, but may be used to increase the surface area of the implant-tissue interface for example for potential drug delivery, increased cellular proliferation (e.g. tissue bulking) or any other application.

The interconnected spheres making up the matrix of the inverse foams described herein can have diameters between about 10 µm and about 2,000 µm, between about 1 µm and about 500 µm, between about 10 µm and about 250 µm, between about 25 µm and about 200 µm, or between about 50 µm and about 100 µm.

In one embodiment, inverse foams in accordance with the invention can be formed by an emulsion process. The process involves combining two compositions in the form of solutions, mixtures, suspensions or emulsions. In one embodiment, two solutions are used. The first composition (composition 1) contains one or more solvents and one or more extractable agents. The second composition (composition 2) contains one or more solvents and one or more matrix agents. The ratio of the composition 1:2 can be varied to obtain the optimal results; the total dissolved solids in each composition may be varied to obtain the optimal results, and the starting component temperatures can be varied to obtain optimal results.

The compositions are then combined, agitated to produce an emulsion or mixture and cast or injected into flat moulds for curing. It will be appreciated by those skilled in the art that the materials in their emulsified form can be used in any end processing application that can be envisioned by a person skilled in the art of coating, lamination or general material or device fabrication. Heat can be optionally applied to the system for curing, or the system may be left to dry at room temperature. Further, the system can be subjected to a vacuum prior to the application of heat. After the removal of the leachable agent(s) by heat and/or vacuum and/or dissolution and/or sublimation, the resulting matrix material is considered cured. If the resulting matrix material cannot maintain its shape without the leachable agent(s), the curing can happen during or before the removal of the leachable agent. The resulting product is an inverse foam.

The emulsion process can be considered a phase inversion process because the two compositions are mixed in a manner which creates a phase inverted emulsion (with respect to a continuous phase of silicone) wherein the silicone phase is in the spherical shape and the leachable phase in the continuous shape. Without wishing to be bound by any particular theory, it is believed that because silicone oils have very low surface tension (high cohesivity in liquid form), it is necessary to decrease the silicone content in the final solution mix in order to create the phase inversion. As the phase inversion occurs, the silicone is in the sphere form and the leachable portion is in the matrix form. However, because of the low surface tension of silicone and its unique ability to readily wet surfaces (as well as high cohesivity), as the emulsion dries and cures, the resulting silicone microspheres become attached to one another thereby forming a network of interconnected spheres. The final form of the material is a solid sheet with a microsphere matrix microstructure.

A surprising feature of the inverse foams described herein is the ratio of total solids. The silicone is in the minority phase compared to the leachable phase. As a result of silicone and its corresponding oils having very low surface tensions, on the order of 21.5 mN/m for a >300 cst fluid, they are very prone to readily wet clean surfaces (for comparative purposes water is 71.97 mN/m at 25° C.). Silicones ability to fully wet most surfaces prevents the use of standard porogens (such as salt sugar or standard emulsions) as matrices for creating a structure that is open enough to be biocompatible and sufficiently open to disorganize the surrounding tissues for the application of preventing or reducing the frequency of capsular contracture. The present inverse foams utilize phase inversion of the emulsion to create interconnections. It has been observed that until phase inversion of the emulsion occurs, the cells of the final foam remain closed. Furthermore, if the emulsion is too dilute, the material falls apart as microspheres. A surprising result of the present foams is that the material falls apart at much lower concentrations of total dissolved solids and matrix/leachable v/v ratios as compared to most conventional materials prepared using this method.

The highly interconnected soft structure of the inverse foams described herein creates the optimal geometry for preventing classical capsular formation around a soft tissue implant. For example, one can construct a set of binary phase diagram with a two component system for each particular configuration of solvent ratios. In such a system, as illustrated in FIG. 1, a desired range can be selected where the matrix agent, or non-leachable component, forms microspheres which are adherent to each other and thereby form a stable structure when the leachable component or agent is extracted. At concentrations of a leachable agent which exceed the desired concentration the material will fall apart as microspheres after the leachable agent is extracted. Conversely, at concentrations where the leachable agent is at lower than desired concentrations a closed cell foam will be created. An individual skilled in the art can envisage such phase diagrams for different materials with appropriate surface tension properties.

In one embodiment described herein are implantable composite members having an external surface at least a portion of which is covered by a foam as described herein. The implantable composite members are made by first providing an implantable shell and providing a foam, for example, an inverse foam comprising a matrix of interconnected spheres of substantially pure silicone. Next, a bonding substance is applied to the foam thereby forming a bondable foam. The bonding substance will act as a means for attaching the foam to the implantable shell. The bondable foam is then applied to at least a portion of the implantable shell and the bonding substance is cured. The curing of the bonding substance adheres the foam to the implantable shell thereby forming a composite material having an external surface at least a portion of which is covered by an foam.

In some embodiments, the bonding substance is room temperature vulcanizing silicone (RTV) or high temperature vulcanizing (HTV) silicone. The bonding substance can be applied to the foams using any method known in the art, for example, brushing, spraying, dipping, curtain coating, vapor deposition methods can be used, casting methods can be used, injection molding and the like. The bonding substance can be cured using heat or any other means of aiding in curing known in the art.

After the foam has been adhered to the surface of the implantable shell, extra portions of foam can be trimmed off to make a relatively smooth edge. In some embodiments, the process is termed lamination.

Foams as described herein can be laminated onto a smooth implant shell using silicone adhesive. The lamination step can be done while the implant is still on the mandrel or on finished implant. The lamination process can utilize a two piece cavity in which a finished smooth implant is pressed between two open celled silicone foam sheets.

For example, the foams can be laminated onto finished smooth implants. A dispersion of HTV silicone is used as the adhesive between the implant and the foam sheets. In the process, the first foam sheet is coated with a thin layer of HTV silicone and then placed in the bottom cavity. The smooth implant is then placed on top of the foam sheet in the cavity. The second foam sheet is coated with a thin layer of HTV silicone and applied on top of the smooth implant. The top piece of the cavity is then fixed in place pressing the two foam sheets together creating a uniform interface. The silicone adhesive is allowed to cure and then the excess foam is cut off creating a uniform seam around the implant.

Another exemplary process involves laminating the foam onto a smooth implant still on a mandrel. In this process a HTV silicone is used as the adhesive between the implant and the foam sheets. The first foam sheet is coated with a thin layer of HTV silicone and then draped over the smooth implant on the mandrel in such a way that there are no wrinkles on the top surface. After this has cured, another coating of HTV silicone is applied and the foam is stretched up to cover part of the back of the implant. The smooth implant is then taken off the mandrel and the excess foam is removed. A smaller circle is cut out of a foam sheet to fit the back of the implant. A thin layer of HTV silicone is applied to the small circle of foam and the circle is attached and allowed to cure.

In another embodiment, a bonding surface is applied to the implant by dipping the implant into HTV silicone and then lamination of the foam onto the implant. The HTV silicone can be applied to the implant using any technique known to those skilled in the art, for example, by spraying curtain coating, and the like.

In yet another embodiment, the implantable shell is coated with an emulsion including an agitated mixture of a first organic solvent and at least one extractable agent, and a second organic solvent and at least one silicone matrix agent. The emulsion can also be applied to the implantable shell. A common method used to coat an implantable shell is to first form the shell itself on a mandrel using a dipping technique and then after the shell is formed, to dip that formed shell into a composition as described herein. The emulsion is then allowed to cure on the implantable shell thereby forming the open celled foam. Extractable materials can then be removed from the open celled foam using various drying and/or leaching techniques known in the art. In one example embodiment, the curing step optionally includes heating.

If the foam is formed on the implantable shell itself, the step of coating and/or applying the emulsion to the implantable shell is accomplished using any method known in the art. For example, spraying, dipping, vapor deposition, brushing, and the like can be used. In an exemplary embodiment, the implantable shell is dipped into an agitated emulsion.

In some embodiments, the foams are applied only to portions of the implantable shell. For example, only the front of the shell is be coated, or only the back of the shell is be coated, or only about 20%, about 30%, about 40%, about 50%, about 60%, about 70% about 80% or about 90% of the shell is coated. In other embodiments, substantially all of the shell is coated.

In one embodiment, the implantable shell is a silicone based shell suitable for use in the manufacture of breast prosthesis or other composite members. The breast prosthesis can be any breast implant known in the art. After applying a foam to a breast prosthesis as described herein, the steps required to make a finished prosthesis may be conventional. First, the opening left by the supporting mandrel is patched with uncured silicone elastomer sheeting. If the prosthesis is to be filled with silicone gel, this gel is added and cured, the filled prosthesis packaged, and the packaged prosthesis sterilized. If the prosthesis is to be inflated with a saline solution, a valve is assembled and installed, the prosthesis is post cured if required, and the prosthesis is then cleaned, packaged and sterilized. A combination silicone/saline mammary prosthesis can also be made.

In other embodiments, the implant can be a pace maker lead, a medical port, catheter, dura mater substitutes, hernia meshes or the like.

The extractable agent, or removable polymer may be, for example, a water soluble material dispersed throughout the curable elastomer. Typical extractable agents or leachable materials may comprise, for example, polyethylene glycol (PEG, also known as polyoxyethylene), polyalkylene oxides including polyethylene oxide and polyethylene oxide/polypropylene oxide copolymers (also known as poloxamers), polyhydroxyethylmethacrylate, polyvinylpyrrolidone, polyacrylamide, or other substituted polyolefins and their copolymers, polylactides, polyglycolides, or other polyesters, polyanhydrides, polyorthoesters and their copolymers, proteins including albumin, peptides, liposomes, cationic lipids, ionic or nonionic detergents, salts including potassium chloride, sodium chloride and calcium chloride, sugars including galactose, glucose and sucrose, polysaccharides including soluble celluloses, heparin, cyclodextrins and dextran, and blends of the same.

When an extractable agent such as PEG is used, the molecular weight of the PEG can be influential on the way the emulsion forms. For example, in one embodiment, the PEG (monomethyl) polymer has a molecular weight of about 2,000 Da. In another embodiment, the PEG polymer has a molecular weight greater than about 750 Da. In some embodiments, the PEG molecular weight ranges from about 1,000 Da to about 100,000,000 Da, or more preferably about 1,000 Da to about 10,000 Da.

In some embodiments, the extractable agent is an agent selected from the group of agents consisting of polyvinyl alcohol, polyethylene glycol, polyethylene oxide, polyacrylic acid; polymethacrylate, poly-lactide, polyglycolide, polycaprolactone, polydioxanone, derivatives thereof, blends thereof, copolymers thereof, terpolymers thereof, and combinations thereof or other biodegradable or non-biodegradable polymers, metals ceramics, composites, or combinations thereof.

The solvent component of the composition can include a solvent selected from the group consisting of xylene, pentane, hexane, dichloromethane (DCM), dimethyl sulfoxide, dioxane, NMP, DMAc, and combinations thereof or any other protic or aprotic solvent or combinations thereof.

EXAMPLE 1

Formulation of Inverse Foams

Table 1 tabulates data for inverse foams prepared according to the methods of the present description. The foams were created as sheets. The formulation components and targets for optimization were total dissolved solids (TDS) in the matrix agent and in the extractable agent solution. TDS upon mixing (e.g. in the emulsion phase), which is highly correlated to viscosity, is important in stabilizing the emulsion. If the TDS are too low, the emulsion is unstable or the micro-geometrically to fine. If the TDS are too high, the emulsion cannot be created without extremely vigorous agitation and/or the micro-geometry is too coarse. Viscosity has its own implications in coating, casting and the like which are known to those skilled in the art. Also important are the ratio of solution 1 to solution 2 and the ratio of the matrix and extractable agents once in solid form. The former is important for affecting surface tension between the phases for proper microstructure formation in the emulsion process, the latter is important for creating the open celled foam structure. This ratio also plays a key role in phase separation of the emulsion.

They were then immediately poured into the desired mold. The volume prepared for casting was varied depending on the size of the mold to obtain foams of varying thicknesses. A standard preparation of this formulation can be 200 mL into a 415 cm$^2$ circular mold to produce a 2 mm thick foam.

TABLE 1

| Name | Extractable Agent | Matrix Agent | Solvent A/Solvent B | Ratio | Theoretical Void Space | Total Dissolved Solvents (%) |
|---|---|---|---|---|---|---|
| F8 | 40% PEG | 40% RTV | DCM/Xylene | 1:2 | 33.33 | 40 |
| F28 | 40% PEG | 40% RTV | DCM/Xylene | 1:1 | 50 | 40 |
| F30 | 40% PEG | 40% RTV | DCM/Xylene | 3:2 | 60 | 40 |
| F31 | 40% PEG | 40% RTV | DCM/Xylene | 2:1 | 66.67 | 40 |
| F33 | 40% PEG | 40% RTV | DCM/Xylene | 3:1 | 75 | 40 |
| F34 | 40% PEG | 40% RTV | DCM/Xylene | 4:1 | 80 | 40 |
| F35 | 60% PEG | 40% RTV | DCM/Xylene | 1:1 | 60 | 50 |
| F36 | 60% PEG | 40% RTV | DCM/Xylene | 2:1 | 75 | 53.33 |
| F38 | 40% PEG | 30% RTV | DCM/Xylene | 2:1 | 72.72 | 36.67 |
| F39 | 60% PEG | 30% RTV | DCM/Xylene | 1:1 | 66.67 | 45 |
| F40 | 60% PEG | 30% RTV | DCM/Xylene | 2:1 | 80 | 50 |
| F41 | 60% PEG | 40% RTV | DCM/Xylene | 3:1 | 81.81 | 55 |
| F42 | 60% PEG | 25% RTV | DCM/Xylene | 3:1 | 87.80 | 51.25 |
| F43 | 60% PEG | 25% RTV | DCM/Xylene | 4:1 | 90.56 | 53 |
| FPV4 | 4% PVA | 25% RTV | H$_2$O/Xylene | 1:1 | 13.8 | 14.5 |
| FPV5 | 4% PVA | 25% RTV | H$_2$O/Xylene | 2:1 | 24.24 | 11 |
| FPV6 | 4% PVA | 25% RTV | H$_2$O/Xylene | 1:2 | 7.41 | 18 |
| FPV7 | 6% PVA | 25% RTV | H$_2$O/Xylene | 1:1 | 19.35 | 15.50 |
| FPV8 | 6% PVA | 25% RTV | H$_2$O/Xylene | 2:1 | 32.43 | 12.33 |
| FPV9 | 6% PVA | 25% RTV | H$_2$O/Xylene | 1:2 | 10.71 | 18.67 |
| FPV12 | 2% PVA | 40% RTV | H$_2$O/Xylene | 1:2 | 2.44 | 27.33 |
| FPV13 | 4% PVA | 40% RTV | H$_2$O/Xylene | 1:1 | 9.09 | 22 |
| FPV15 | 4% PVA | 40% RTV | H$_2$O/Xylene | 1:2 | 4.76 | 28.00 |
| FPV16 | 6% PVA | 40% RTV | H$_2$O/Xylene | 1:1 | 13.04 | 23 |
| FPV18 | 6% PVA | 40% RTV | H$_2$O/Xylene | 1:2 | 6.98 | 28.67 |
| FPVA4 | 4% PVA | 25% RTV | H$_2$O/DCM | 1:1 | 13.79 | 14.50 |
| FPVA7 | 6% PVA | 25% RTV | H$_2$O/DCM | 1:1 | 19.35 | 15.5 |

EXAMPLE 2

Formation of an Inverse Foam

Foam F35 from Table 1 has a theoretical void space of 60% and was prepared using a 1:1 ratio of 60% polyethylene glycol monomethyl ether (PEG) by weight in dichloromethane and 40% MED-1037 adhesive silicone by weight in xylene. The silicone and PEG dispersions were mixed at equal volumes and vigorously shaken by hand for 30 seconds.

EXAMPLE 3

Formation of an Additional Inverse Foam

Foam F41 from Table 1 has a theoretical void space of 81.81% and was prepared using a 3:1 ratio of 60% PEG by weight in dichloromethane and 40% MED-1037 adhesive silicone by weight in xylene. The silicone and PEG dispersions were mixed at the ratio of 3 parts PEG to 1 part silicone and vigorously shaken by hand for 30 seconds. They were then immediately poured into the desired mold. A standard preparation of this formulation is 200 mL into a 415 cm$^2$ circular mold to produce a 2 mm foam.

EXAMPLE 4

Formation of an Additional Inverse Foam

Foam F42 from Table 1 has a theoretical void space of 87.8% and was prepared using a 1:1 ratio of 60% PEG by weight in dichloromethane and 25% MED-1037 adhesive silicone by weight in xylene. The silicone and PEG dispersions were mixed at the ratio of 3 parts PEG to 1 part silicone and vigorously shaken by hand for 30 seconds. They were then immediately poured into the desired mold. A standard preparation of this formulation is 400 mL into a 415 cm$^2$ circular mold to produce a 2 mm foam.

Figure 6B:
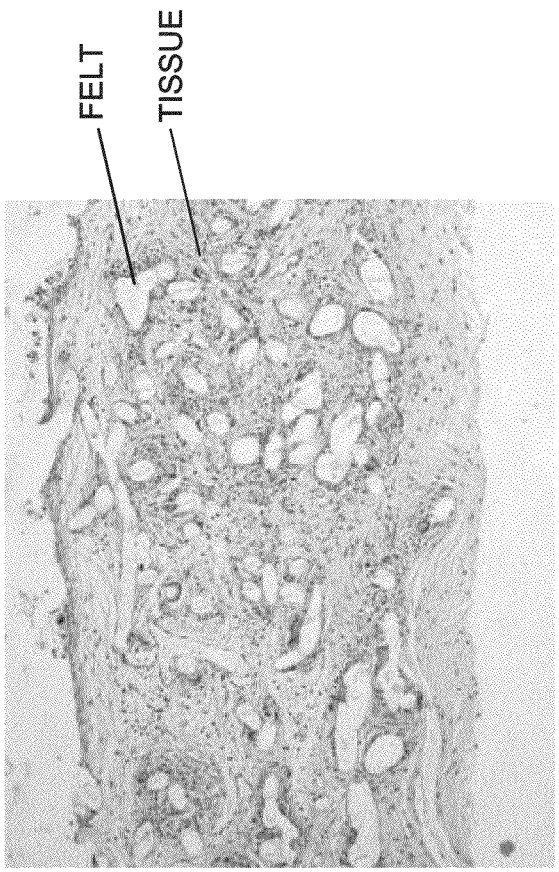
FIG. 6B is a histological image tissue ingrowth into the open cell foam 6 weeks after subcutaneous implantation in a rat.
Figure 6A:
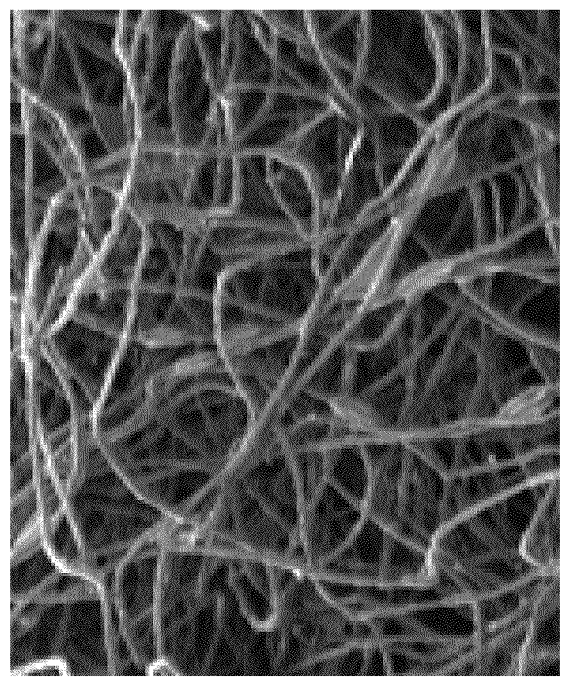
FIG. 6A is a SEM image at a scale of 0-600 µm of a fibrous felt according to an example embodiment described herein.

Still another type of material which can attain an optimal biological response is a fibrous felt. In one embodiment, the fibrous felt material comprises polypropylene. A scanning electron microscope (SEM) image of an exemplary fibrous felt is depicted in FIG. 6A; a histological image is depicted in FIG. 6B. Such exemplary fibrous felts can have a pore size from about 10 µm to about 300 µm, or about 15 µm to about 200 µm, or about 20 µm to about 120 µm. In one embodiment, the pore size is about 23 µm to about 102 µm. The fibrous felts can have an interconnection size of about 75 µm to about 300 µm, or about 100 µm to about 270 µm, or about 150 to about 250 µm. In one embodiment, the interconnection size is about 159 µm to about 225 µm.

The materials can described herein which can attain an optimal biological response have porosities in the range of about 65% to about 99%, or about 67% to about 98%. Further, the materials described herein can be applied to the surface of an implant. The thickness of material applied to an implant generally is from about 1.0 to 6.0 mm, or from about 1.5 mm to about 5.0 mm. Thicknesses of can be about 1.5 mm, about 2.0 mm, about 2.5 mm, about 3.0 mm, about 3.5 mm, about 4.0 mm, about 4.5 mm, or about 5.0 mm. Depending on the thickness of the material, a resulting stiffness will be exhibited. Exemplary stiffness includes a range from about 4.0 KPa to about 15.0 KPa, or about 4.5 KPa to about 14.0 KPa, or about 4.7 KPa to about 13.2 KPa. The stiffness can be about 5.0 KPa, about 6.0 KPa, about 7.0 KPa, about 8.0 KPa, about 9.0 KPa, about 10.0 KPa, about 11.0 KPa, about 12.0 KPa, or about 13.0 KPa.

The materials described herein are generally made by preparing one or more solutions containing a matrixing agent and/or a leachable or extractable agent. The solutions can first be mixed and emulsified. Then, the emulsified solution is cast, cured and leached. In some embodiments, the solutions are cast over or within a mold or template of appropriate shape. In one embodiment, the materials are cast as sheets which can be easily cut to a desired shape.

Figure 7:
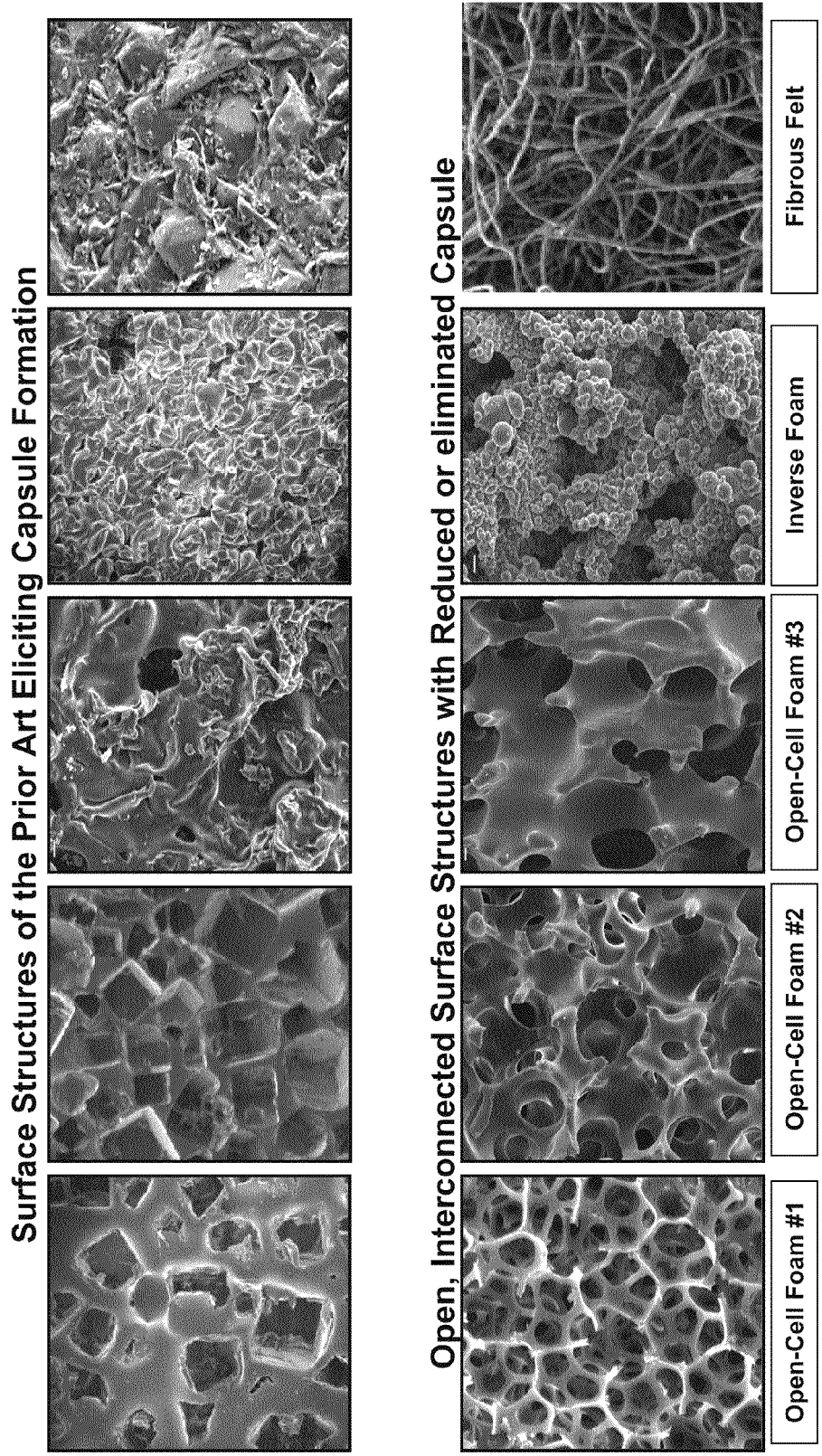
FIG. 7 illustrates various SEM images at a scale of 0-600 µm of textures of the prior art and textures according to the present invention.

FIG. 7 illustrates various textures of the PRIOR ART which elicit capsule formation and various textures according to the present invention that reduce or eliminate capsule formation.

In one embodiment described herein are implantable composite members having an external surface at least a portion of which is covered by a material as described herein which can attain an optimal biological response. The materials can impart the optimal biological response to the implantable member. The implantable composite members are made by first providing an implantable member (e.g., an implantable shell or implantable medical device) and providing a material as described herein. Next, a bonding substance is applied to a chosen material, thereby forming a bondable material. The bonding substance will act as a means for attaching the material to the implantable member. The bondable material is then applied to at least a portion of the implantable member and the bonding substance is cured. Alternatively, the bonding substance can be applied directly to implantable member, and not to the material. The curing of the bonding substance adheres the material to the implantable member thereby forming a composite member having an external surface at least a portion of which is covered by one or more of the materials described herein.

In some embodiments, the bonding substance is room temperature vulcanizing silicone (RTV) or high temperature vulcanizing (HTV) silicone. The bonding substance can be applied to the foam or felt described herein using any method known in the art, for example, brushing, spraying, dipping, curtain coating, vapor deposition methods can be used, casting methods can be used, injection molding and the like. The bonding substance can be cured using heat or any other means of aiding in curing known in the art.

After the material has been adhered to the surface of the implantable member, extra portions can be trimmed off to make a relatively smooth edge. In some embodiments, the process is termed lamination.

For example, the materials can be laminated onto finished smooth implants (e.g., a breast implant) within a cast. A dispersion of HTV silicone is used as the adhesive between the implant and the sheets of material. In the process, the first sheet is coated with a thin layer of HTV silicone and then placed in the bottom cavity. The smooth implant is then placed on top of the sheet in the cavity. The second sheet is coated with a thin layer of HTV silicone and applied on top of the smooth implant. The top piece of the cavity is then fixed in place pressing the two sheets together creating a uniform interface. The silicone adhesive is allowed to cure and then the excess material is cut off creating a uniform seam around the implant.

Another exemplary process involves laminating foam or felt onto a smooth implant still on a mandrel. In this process HTV silicone is used as the adhesive between the implant and sheets of appropriate material. A first sheet is coated with a thin layer of HTV silicone and then draped over the smooth implant on the mandrel in such a way that there are no wrinkles on the top surface. After this has cured, another coating of HTV silicone is applied and the sheet is stretched up to cover part of the back of the implant. The smooth implant is then taken off the mandrel and the excess material is removed. A smaller circle is cut out of a sheet to fit the back of the implant. A thin layer of HTV silicone is applied to the small circle and the circle is attached and allowed to cure.

In another embodiment, a bonding surface is applied to the smooth implant by dipping the implant into HTV silicone and then lamination of material onto the implant. The HTV silicone can be applied to the implant using any technique known to those skilled in the art, for example, by spraying curtain coating, and the like.

If one of the materials described herein is formed directly on an implant, for example a composite shell such as a breast implant, the step of coating and/or applying the material to the composite shell is accomplished using any method known in the art. For example, spraying, dipping, vapor deposition, brushing, and the like can be used. In an exemplary embodiment, the implantable shell is dipped into an agitated emulsion and the material is allowed to cure directly on the implant.

In some embodiments, the materials can be applied only to portions of the implantable member. For example, only the front of the implantable member is be coated, or only the back of the implantable member is be coated, or only about 20%, about 30%, about 40%, about 50%, about 60%, about 70% about 80% or about 90% of the implantable member is coated. In other embodiments, substantially all of the implantable member is coated.

In one embodiment, the implantable member is a silicone based shell suitable for use in the manufacture of breast prosthesis or other composite members. The breast prosthesis can be any breast implant known in the art. After applying a material as described herein to a breast prosthesis, the steps required to make a finished prosthesis may be conventional. First, the opening left by the supporting mandrel is patched with uncured elastomer sheeting. If the prosthesis is to be filled with silicone gel, this gel is added and cured, the filled prosthesis packaged, and the packaged prosthesis sterilized. If the prosthesis is to be inflated with a saline solution, a valve is assembled and installed, the prosthesis is post cured if required, and the prosthesis is then cleaned, packaged and sterilized. A combination silicone/saline mammary prosthesis can also be made.

In other embodiments, the implantable member can be a pace maker lead, a medical port, catheter, dura mater substitutes, hernia meshes or the like.

The presently described materials provide soft tissue implants with the ability for tissue ingrowth into the voids within the materials once implanted. This tissue ingrowth prevents or substantially prevents the formation of a capsule around a soft tissue implant. Hence, contracture of a capsule formed around a soft tissue implant and associated bleeding is avoided using the materials described herein. Thus, implants comprising the materials described herein may provide relief from contracture pain from capsules surrounding the implants.

A method has been described for creating an outer layer having at least one of the materials described herein. Further, the method can be applied to create a medical implant with an external surface layer of a foam and/or felt as described herein for use in creating strips having a textured surface for control of scar formation, or to improve a process for making mammary prostheses. The product made by this method has utility in preventing capsular contraction, in preventing or controlling scar formation, and in anchoring medical implants.

Scar tissue formation in the healing of a wound or surgical incision is also a process involving the growth of fibrous tissue. A visible scar results from this healing process because the fibrous tissue is aligned in one direction. However, it is often aesthetically desirable to prevent or significantly reduce classical scar formation, especially in certain types of plastic surgery. A member having one or more of the materials described herein on its surface can be placed subcutaneously within a healing wound or incision to prevent the fibrous tissue from aligning and thereby prevent or reduce scar formation.

Even further, it is often important to anchor medical implants to prevent their movement, displacement or rotation. Mammary prostheses are one example of implants that are preferentially anchored. Facial implants are another example of implants that can be anchored. With facial implants, for example, it is important that they be anchored securely against movement because of their prominent location. Providing such implants with foam or felt surface made in accordance with the present description is an advantageous way to ensure that they will be anchored securely as tissue ingrowth once implanted will prevent their migration.

EXAMPLE 5

Comparison of Previous Implant Textures with the Present Materials

FIG. 7 illustrates various SEM images at a scale of 0-600 µm of textures of the prior art (upper row) and textures suitable for achieving an optimal tissue response.

Figure 8:
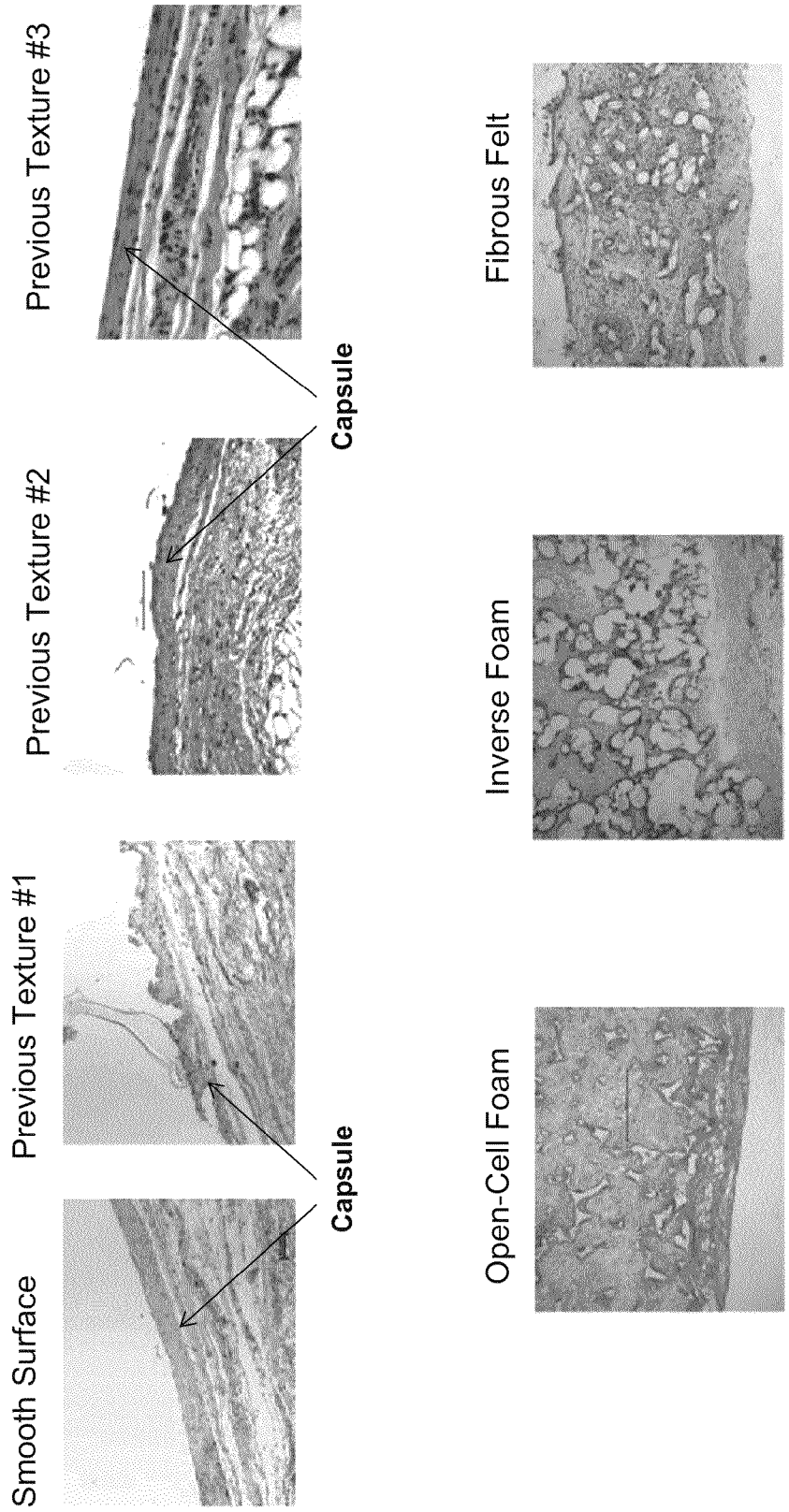
FIG. 8 illustrates a histological image comparison of materials described herein with textured materials known in the art.

As illustrated in FIG. 8, histological samples in a rat model demonstrate that textures of the current invention show little or no capsule formation at the surface of the implant. In comparison, the smooth implant and commercial textured implants in the upper row of FIG. 8 all exhibit significant capsule formation.

Figure 9:
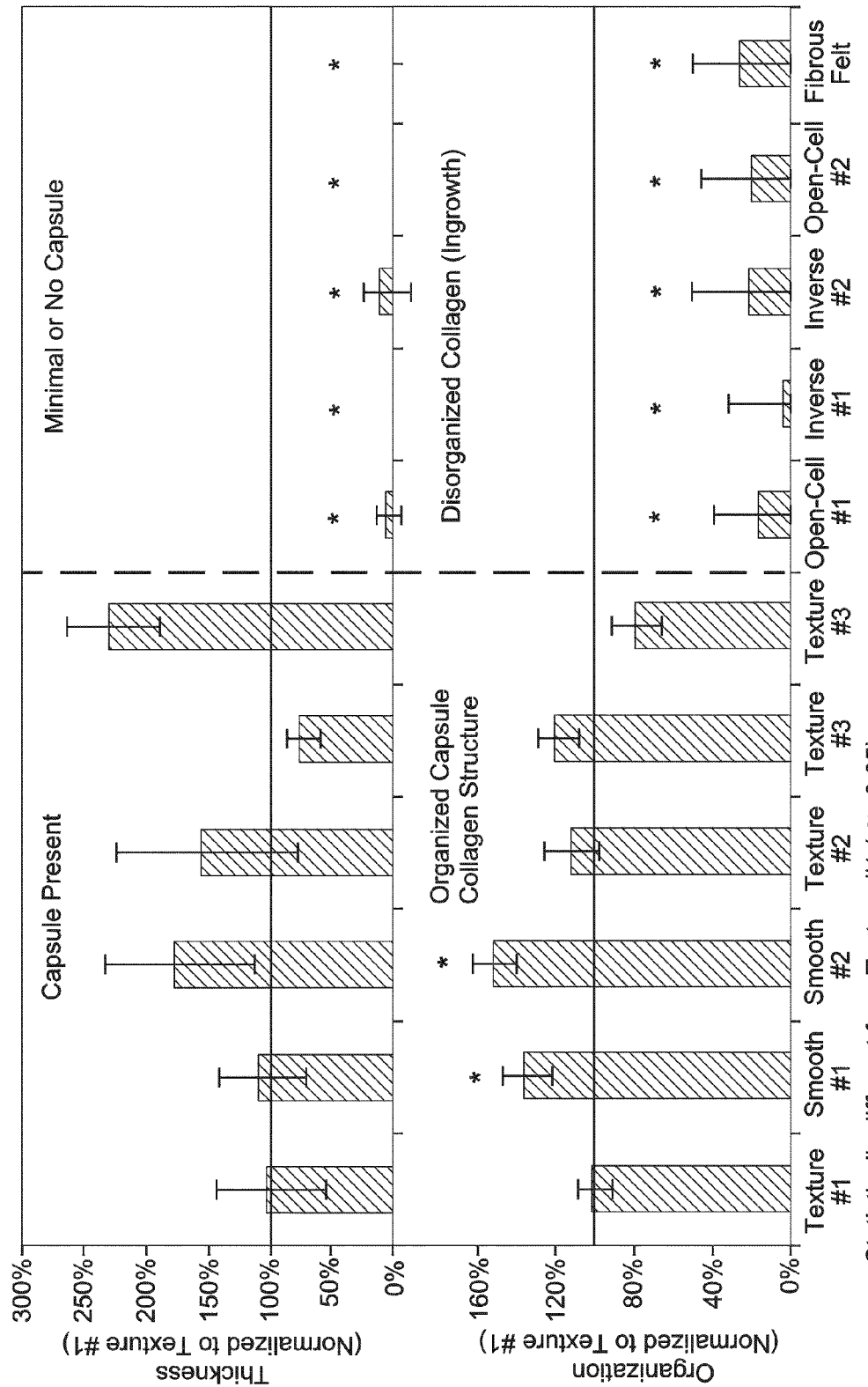
FIG. 9 graphically illustrates a capsule thickness and collagen fiber organization comparison between materials described herein with textured materials known in the art. The capsule thickness and collagen fiber organization data is normalized to the data obtained with previous Texture #1. Organization of collagen fibers is assessed by evaluating the variance of the angle of the fibers to the surface of the implant.

FIG. 9 graphically illustrates the percent thickness of capsule formation around a soft tissue implant and percent organization of a capsule. It is believed that the capsule is largely collagen. The materials of the present invention exhibit minimal or no capsule formation and disorganized tissue around the implant ingrown into the texture. Previous textures have capsules present and the capsule is, in some cases, highly organized (e.g., on a smooth surface).

Figure 10:
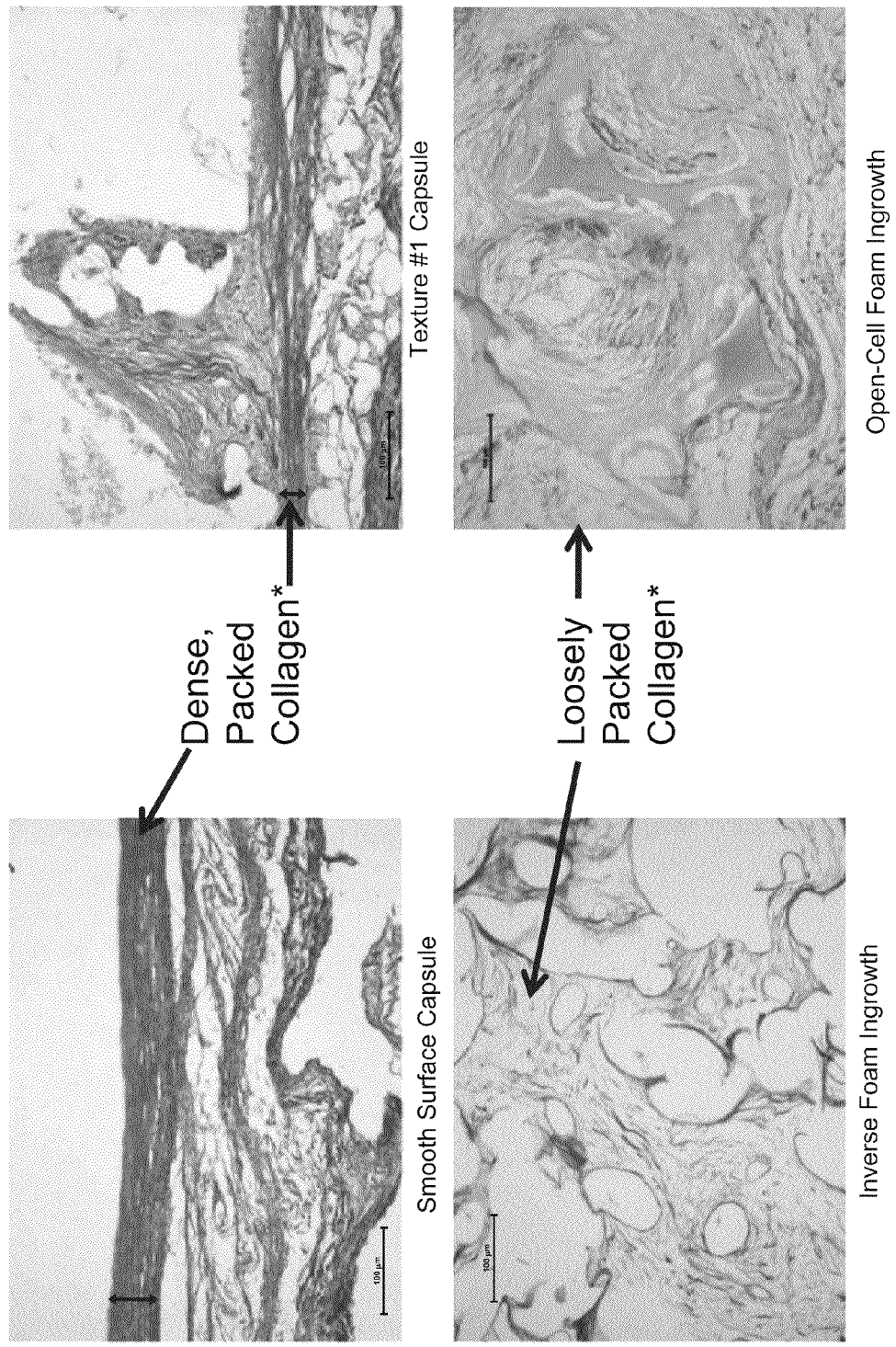
FIG. 10 illustrates histological images comparing capsule collagen formation around and within materials described herein and textured materials known in the art.
Figure 11:
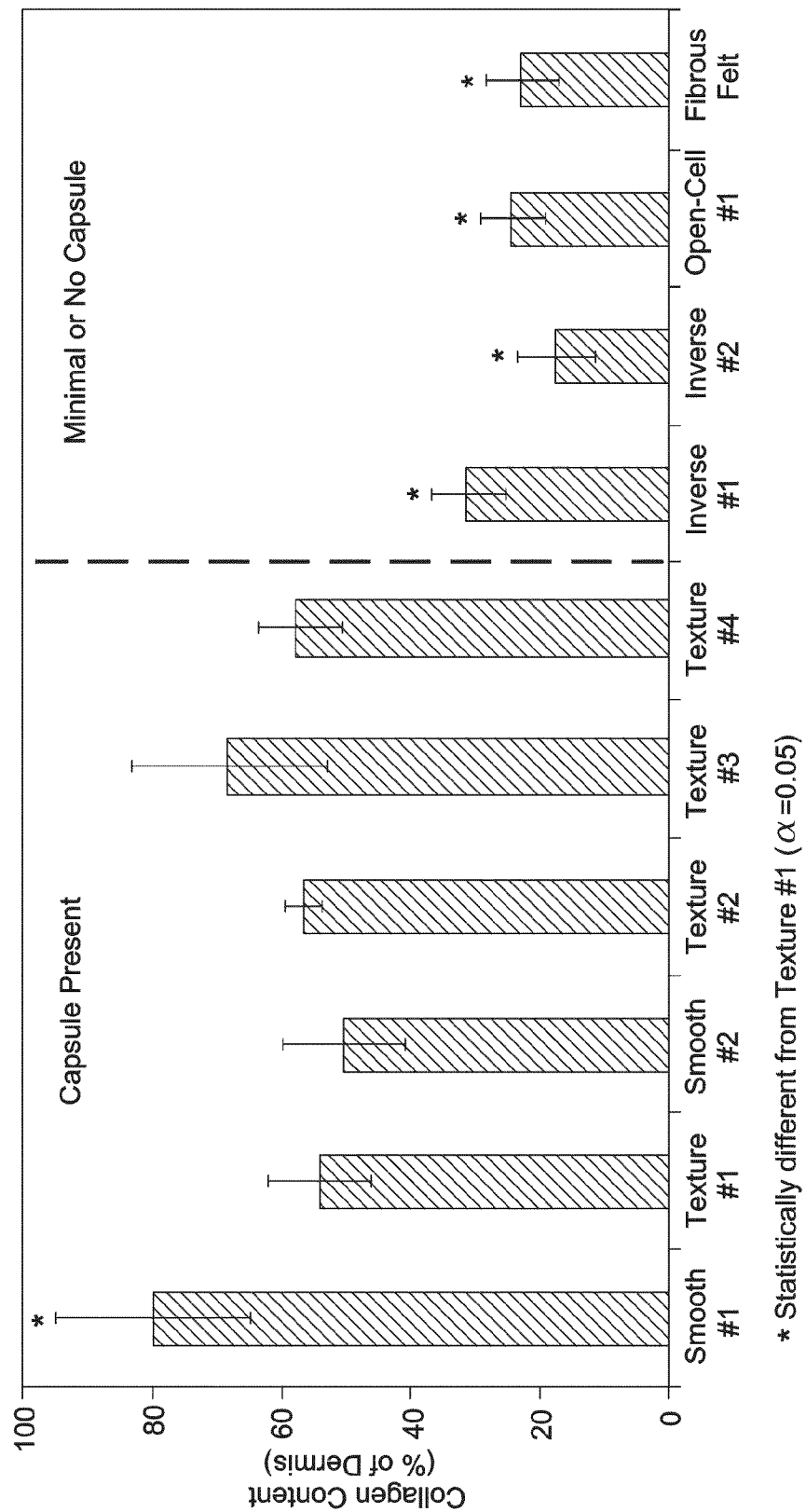
FIG. 11 graphically compares the adjacent tissue/capsule collagen content in the rat model between materials described herein with textured materials known in the art.

FIG. 10 illustrates histological samples wherein densely packed collagen capsules are present in both smooth surface and Texture #1 samples. The histological samples of both open-celled foam and polyurethane foam illustrate that only loosely packed, disorganized collagen surrounds the foams. FIG. 11 graphically illustrates that open-cell foams, inverse foams and fibrous felt described herein decrease collagen density within capsules and that tissue ingrowth shows a very loose collagen network.

Figure 12:
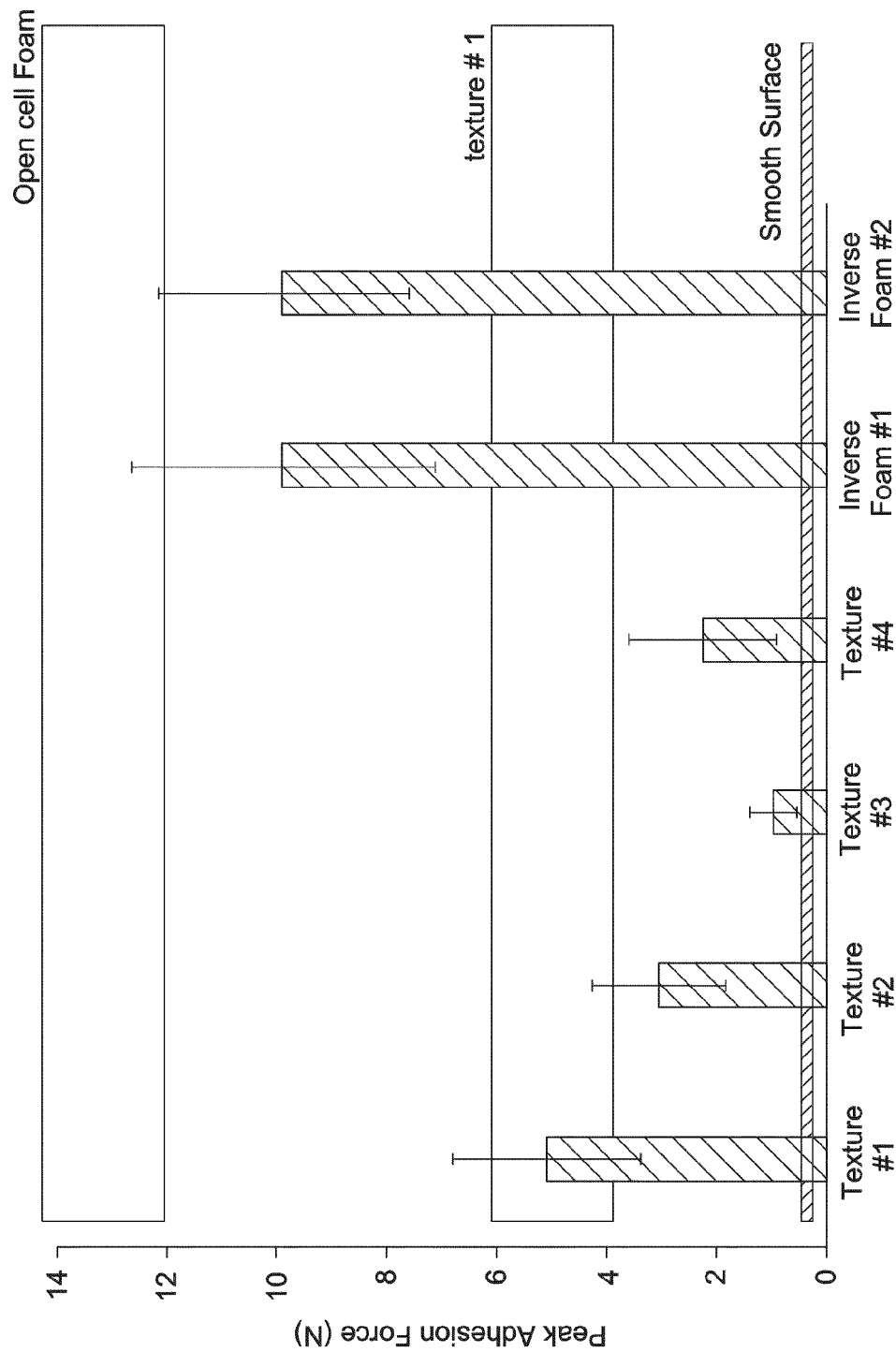
FIG. 12 graphically illustrates an adhesion to surrounding tissues comparison between materials described herein with textured materials known in the art. Data is expressed as the mechanical force to separate tissue from the material. Shaded, horizontal bars show the range of multiple studies with smooth, Texture #1, and, open cell foam #1, as indicated.

Adhesion of the implants to the surrounding tissues is also evaluated. FIG. 12 graphically illustrates that open-cell foams of the present invention adhere to tissues on average twice a tightly as any previous texture and on average ten times as much as a smooth surface implant.

Figure 13:
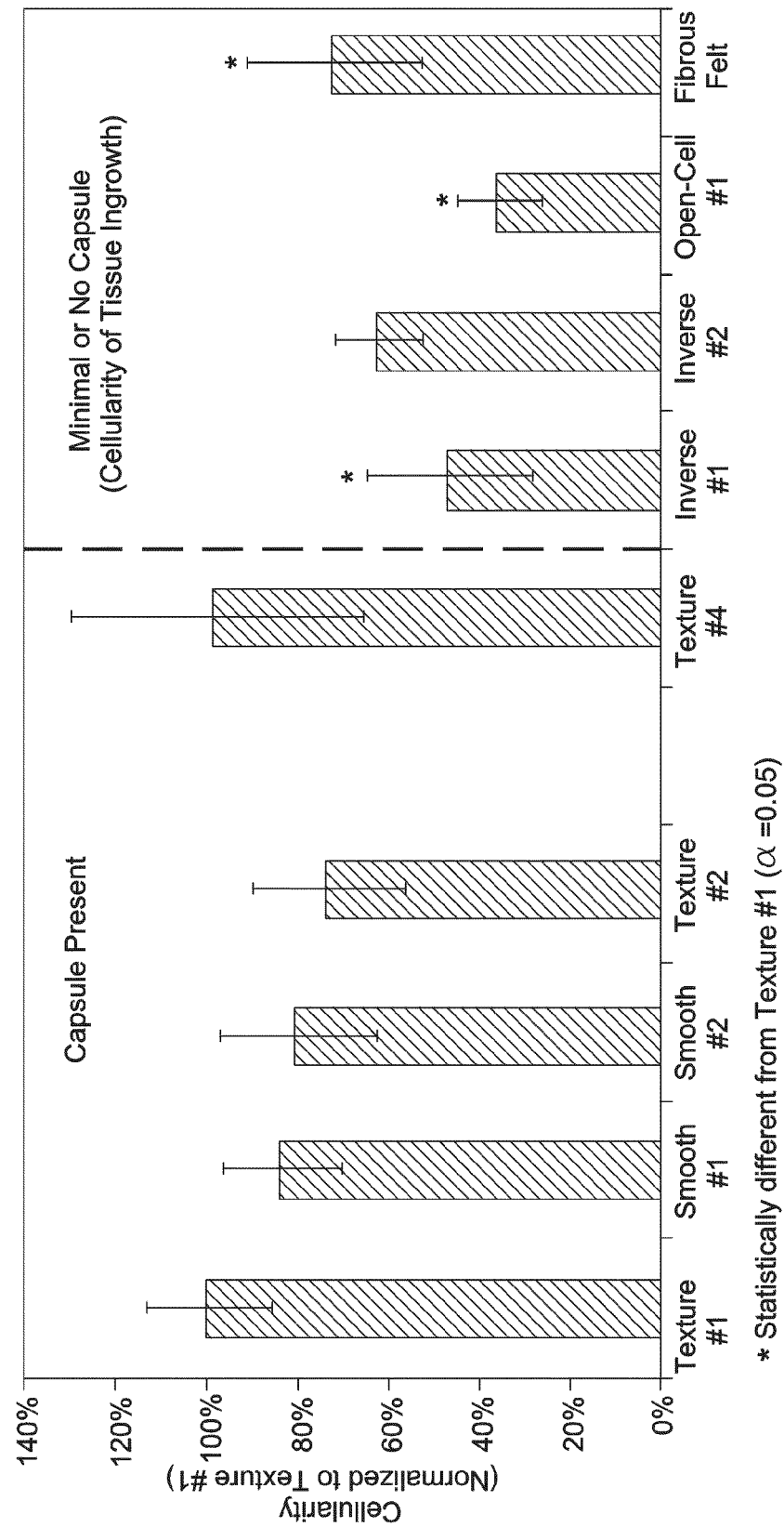
FIG. 13 illustrates the cell density around an implant measured at 6 weeks (n=6) in tissue around an implant in rat model.

FIG. 13 illustrates the cell density around an implant measured at 6 weeks (n=6). Materials that do not result in capsule show tissue ingrowth with lower cell density.

FIG. 14 illustrates the temporal changes in a capsule or tissue ingrowth surrounding an implant. The thickness of the capsule and ingrowth does not change appreciably from 6 to 16 weeks post-implantation in a rat model. However, the organization of the capsule increases and remains constant in the tissue ingrowth in the same time period. Cellularity decreases in the same time period but remains constant with ingrowth.

FIGS. 7 through 14 demonstrate that some of the materials of the present invention reduce or eliminate capsule formation around an implant (e.g., soft tissue implant), create a disorganized tissue within the void spaces of the materials and adhere better to surrounding tissues than previous textured surfaces known in the art.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A breast implant comprising:
   a fillable or inflatable elastomeric shell having an internal surface and an external surface; and
   a foam bonded to the external surface of the shell, the foam being substantially pure silicone in the form of a network of interconnected silicone microspheres wherein interconnections between microspheres are formed by a phase inversion emulsion process;
   the foam having a pore size of 400 μm to 550 μm and an interconnection size of 150 μm to 300 μm.

2. The breast implant according to claim 1 wherein said pore size is 470 μm.

3. The breast implant according to claim 1 wherein said interconnection size is 210 μm.

4. A soft tissue implant comprising:
   a fillable or inflatable elastomeric shell having an internal surface and an external surface; and
   a foam bonded to the external surface of the shell, the foam being substantially pure silicone in the form of a network of interconnected silicone microspheres wherein interconnections between microspheres are formed by a phase inversion emulsion process;
   the foam having a pore size of 400 μm to 550 μm and an interconnection size of 150 μm to 300 μm.

* * * * *

UNITED STATES PATENT AND TRADEMARK OFFICE
CERTIFICATE OF CORRECTION

PATENT NO. : 9,072,821 B2  
APPLICATION NO. : 13/021615  
DATED : July 7, 2015  
INVENTOR(S) : Dennis E. Van Epps et al.

It is certified that error appears in the above-identified patent and that said Letters Patent is hereby corrected as shown below:

In column 16, line 23, in claim 1, delete "microspheres" and insert -- microspheres, --, therefor.

In column 16, line 37, in claim 4, delete "microspheres" and insert -- microspheres, --, therefor.

Signed and Sealed this  
First Day of December, 2015

Michelle K. Lee  
*Director of the United States Patent and Trademark Office*